United States Patent
Hammerland et al.

(10) Patent No.: US 10,345,292 B2
(45) Date of Patent: Jul. 9, 2019

(54) MAMMALIAN CELL LINES EXPRESSING FUNCTIONAL NEMATODE ACETYLCHOLINE RECEPTORS AND USE THEREOF FOR HIGH-THROUGHPUT SCREENING ASSAYS

(71) Applicants: MERIAL, INC., Duluth, GA (US); Sanofi, Paris (FR)

(72) Inventors: Lance Hammerland; Brenda Bondesen, Atlanta, GA (US); Jean-Marie Chambard, Yerres (FR); Thierry Vermat, Chazay d'Azergues (FR); Werner Dittrich, Frankfurt (DE); Michel Partiseti, Bourg la Reine (FR); Qing Zhou-Liu, Chennevieres sur Marne (FR); Cathy Cojean, Massy (FR); Rachid Boukaiba, Cretail (FR); Eric Tagat, Sucy en Brie (FR)

(73) Assignees: BOEHRINGER INGELHEIM ANIMAL HEALTH INC., Duluth, GA (US); SANOFI, Paris (FR)

( * ) Notice: Subject to any disclaimer, the term of this patent is extended or adjusted under 35 U.S.C. 154(b) by 0 days.

(21) Appl. No.: 14/849,446

(22) Filed: Sep. 9, 2015

(65) Prior Publication Data

US 2017/0067873 A1 Mar. 9, 2017

Related U.S. Application Data

(60) Provisional application No. 62/047,822, filed on Sep. 9, 2014.

(51) Int. Cl.
| | |
|---|---|
| C07K 14/47 | (2006.01) |
| G01N 33/50 | (2006.01) |
| C07K 14/435 | (2006.01) |
| G01N 33/68 | (2006.01) |
| C07K 14/705 | (2006.01) |
| C12N 5/071 | (2010.01) |

(52) U.S. Cl.
CPC ....... *G01N 33/502* (2013.01); *C07K 14/4354* (2013.01); *C07K 14/4705* (2013.01); *C07K 14/70571* (2013.01); *C12N 5/0602* (2013.01); *G01N 33/6872* (2013.01); *C12N 2503/02* (2013.01); *C12N 2510/00* (2013.01); *G01N 2333/4353* (2013.01); *G01N 2333/4706* (2013.01); *G01N 2500/10* (2013.01)

(58) Field of Classification Search
None
See application file for complete search history.

(56) References Cited

U.S. PATENT DOCUMENTS

| 6,087,160 A | 7/2000 | Yuan et al. |
| 2004/0038875 A1 | 2/2004 | Greenfield et al. |
| 2004/0224910 A1 | 11/2004 | Sattelle et al. |
| 2008/0260750 A1 | 10/2008 | Dent et al. |
| 2010/0212029 A1* | 8/2010 | Orr ...................... C07K 16/286 800/3 |
| 2012/0172346 A1 | 7/2012 | Di Paolo et al. |

OTHER PUBLICATIONS

Boulin et al. (2011) Functional reconstitution of Haemonchus contortus acetylcholine receptors in Xenopus oocytes provides mechanistic insights into levamisole resistance. British Journal of Pharmacology, 164:1421-1432.*
Bennett et al. (2012) Xenopus laevis RIC-3 enhances the functional expression of the C. elegans hommeric nicotinic receptor, ACR-16, in Xenopus oocytes. Journal of Neurochemistry, 123:911-918.*
Slimko et al. (2003) Codon optimization of Caenorhabditis elegans GluCl ion channel genes for mammalian cells dramatically improves expression levels. Journal of Neuroscience Methods, 124:75-81.*
EU051823.1 (Haemonchus contortus nicotinic acetylcholine receptor 16 mRNA, complete cds, GenBank Reference Sequence, priority to Jan. 1, 2008, 2 pages).*
NM_024557.4 (*Homo sapiens* RIC3 acetylcholine receptor chaperone (RIC3), transcript variant 1, mRNA, NCBI Reference Sequence, priority to Aug. 8, 2013, 6 pages).*
Wolstenholme, A. (2011) Ion channels and receptor as targets for the control of parasitic nematodes. International Journal for Parasitology: Drugs and Drug Resistance 1:2-13 (Year: 2011).*
Chambard et al. Transforming TRP Channel Drug Discovery Using Medium-Throughput Electrophysiological Assays. Journal of Biomolecular Screening 2014, vol. 19(3) 468-477.
Hayley etal. *Xenopus laevis* RIC-3 enhances the functional expression of the *C. elegans* homomeric nicotinic receptor, ACR-16, in *Xenopus oocytes*. J. Neurochem. (2012) 123, 911-918.
Invitrogen reference. Product manual for pcDNA™5/FRT/TO—Inducible expression vector designed for use with the Flp-In™ T-REx™ System. Dated Nov. 11, 2010.
Lee et al. Parasitic Helminths: Targets, Screens, Drugs and Vaccines, First Edition. Edited by Conor R. Caffrey 2012 Wiley-VCH Verlag GmbH & Co. KGaA. Published 2012 by Wiley-VCH Verlag GmbH & Co. KGaA.
Lemmens et al. Heteromeric MAPPIT: a novel strategy to study modification-dependent protein-protein interactions in mammalian cells. Nucleic Acids Research, 2003, vol. 31, No. 14 e75.
Roncarati et al. Functional Properties of 7 Nicotinic Acetylcholine Receptors Co-expressed with RIC-3 in a Stable Recombinant CHO-K1 Cell Line. Assay and Drug Development Technologies vol. 6, No. 2, 2008.

* cited by examiner

*Primary Examiner* — Neil P Hammell
(74) *Attorney, Agent, or Firm* — Judy Jarecki-Black; Steffan Finnegan

(57) ABSTRACT

The following discloses mammalian cells lines that stably express functional nematode acetylcholine receptor subunits. The resulting expression of functional ion channels has been made possible by the stable co-expression of the chaperone protein, RIC3. These cell lines are extremely useful for the high throughput screening (HTS) of compounds, to identify new candidate parasiticidal, including nematocidal, active ingredients.

7 Claims, 11 Drawing Sheets

Specification includes a Sequence Listing.

FIG. 2

```
                        SEQUENCE LISTING

<160> NUMBER OF SEQ ID NOS: 33

<210> SEQ ID NO 1
<211> LENGTH: 1482
<212> TYPE: DNA
<213> ORGANISM: Artificial Sequence
<220> FEATURE:
<223> OTHER INFORMATION: Hco ACR-16 (Accession number for Hco ACR-16 is
      EU051823.1)

<400> SEQUENCE: 1
atgtggagct tgctgatcgc ctgctcattc gttgctgttg cggttgttat tgcctcgtat     60
gacgagcggc gtctgtatga ggatctcatg agggactaca acagtctcga acggccagtg    120
gccaaccatt caaagccagt taccgtatat ctaaaggttt ctcttcaaca gatcatcgat    180
gtcgacgaga aaatcaaat agttcatgtg aacgcatggc ttgactacac atggaaggat     240
tacaaacttg tatgggatgt cagcgaatat gggaacataa cggacgtgcg atttcctgct    300
ggtagaattt ggaaaccaga cgtgctgctc tacaacagcg ttgacacgaa ctttgattcg    360
acctatccta caaacatggt cgtgtacagc actggtgatg tacattgggt accaccgggt    420
atcttcaaga tttcctgtaa aattgacatc gagtggttct ctttcgatga gcaacgttgc    480
aaattcaagt ttggttcatg gacttacgac ggattcaaac ttgatctaca gcctgccaaa    540
aaaggattcg acatttctga gtacttgccg aacggagagt ggacattacc tttgactact    600
gtctcacgaa acgtgaagtt ctacgattgc tgtcccgaac catatccgga tctgacattc    660
tacttgcata tgcggaggcg aactctctac tacggattca acctcatcat gccatgtatt    720
cttacaacac tcatgacctt acttggtttc actttaccac ctgatgctgg agagaaaatc    780
actttgcaga ttactgtatt gctttccatt tgtttcttct tgagtatcgt ttccgagatg    840
tcacctccaa cgtcggaagc tgttccactt ctaggaatat tcttcacatg ctgcatgatt    900
gttgttactg catctcacgg tattcacggtc tacgtactca atcttcacta tagaacgcca   960
gaaactcacg aaatgactcc cgtgatgcgt tcagtactcc tgtattggtt gccatggatg   1020
ctgcgcatga aacgaccagg tgtcaaactc acttacgcaa cacttccgtc tctgttcaac   1080
ttgaaactca aaagtcattc ggagtctctg attagaaata tcaaggaaaa tgagtccagc   1140
acctctaggt cgaattctct ggacatagag cgacgtcttc attactacat gtcttcatca   1200
gggcttatga atggcatttc accttcaact gcgttgccac agactcagat ttccgctcct   1260
ttagatcttg gacaacaagc aacactgctt atactgcaac ggatttacca agaattgaag   1320
gttgtaacaa agcggatgat ggagacagac agggaggggc aggcatcgaa taactggaag   1380
tttgcggcaa tggttgtgga caggctgtgc ctctacgtct tcacgatgtt catcttggcg   1440
tcaaccatcg gaatcttctc ctcggctcca tatctggtcg cc                      1482

<210> SEQ ID NO 2
<211> LENGTH: 494
<212> TYPE: PRT
<213> ORGANISM: Artificial Sequence
<220> FEATURE:
<223> OTHER INFORMATION: Hco ACR-16 protein (translation of SEQ ID NO:1)

<400> SEQUENCE: 2

Met Trp Ser Leu Leu Ile Ala Cys Ser Phe Val Ala Val Ala Val Val
1               5                   10                  15
```

-continued

```
Ile Ala Ser Tyr Asp Glu Arg Arg Leu Tyr Glu Asp Leu Met Arg Asp
            20                  25                  30

Tyr Asn Ser Leu Glu Arg Pro Val Ala Asn His Ser Lys Pro Val Thr
        35                  40                  45

Val Tyr Leu Lys Val Ser Leu Gln Gln Ile Ile Asp Val Asp Glu Lys
    50                  55                  60

Asn Gln Ile Val His Val Asn Ala Trp Leu Asp Tyr Thr Trp Lys Asp
65                  70                  75                  80

Tyr Lys Leu Val Trp Asp Val Ser Glu Tyr Gly Asn Ile Thr Asp Val
                85                  90                  95

Arg Phe Pro Ala Gly Arg Ile Trp Lys Pro Asp Val Leu Leu Tyr Asn
            100                 105                 110

Ser Val Asp Thr Asn Phe Asp Ser Thr Tyr Pro Thr Asn Met Val Val
        115                 120                 125

Tyr Ser Thr Gly Asp Val His Trp Val Pro Pro Gly Ile Phe Lys Ile
    130                 135                 140

Ser Cys Lys Ile Asp Ile Glu Trp Phe Ser Phe Asp Glu Gln Arg Cys
145                 150                 155                 160

Lys Phe Lys Phe Gly Ser Trp Thr Tyr Asp Gly Phe Lys Leu Asp Leu
                165                 170                 175

Gln Pro Ala Lys Lys Gly Phe Asp Ile Ser Glu Tyr Leu Pro Asn Gly
            180                 185                 190

Glu Trp Thr Leu Pro Leu Thr Thr Val Ser Arg Asn Val Lys Phe Tyr
        195                 200                 205

Asp Cys Cys Pro Glu Pro Tyr Pro Asp Leu Thr Phe Tyr Leu His Met
    210                 215                 220

Arg Arg Arg Thr Leu Tyr Tyr Gly Phe Asn Leu Ile Met Pro Cys Ile
225                 230                 235                 240

Leu Thr Thr Leu Met Thr Leu Leu Gly Phe Thr Leu Pro Pro Asp Ala
                245                 250                 255

Gly Glu Lys Ile Thr Leu Gln Ile Thr Val Leu Leu Ser Ile Cys Phe
            260                 265                 270

Phe Leu Ser Ile Val Ser Glu Met Ser Pro Pro Thr Ser Glu Ala Val
        275                 280                 285

Pro Leu Leu Gly Ile Phe Phe Thr Cys Cys Met Ile Val Val Thr Ala
    290                 295                 300

Ser Thr Val Phe Thr Val Tyr Val Leu Asn Leu His Tyr Arg Thr Pro
305                 310                 315                 320

Glu Thr His Glu Met Thr Pro Val Met Arg Ser Val Leu Leu Tyr Trp
                325                 330                 335

Leu Pro Trp Met Leu Arg Met Lys Arg Pro Gly Val Lys Leu Thr Tyr
            340                 345                 350

Ala Thr Leu Pro Ser Leu Phe Asn Leu Lys Leu Lys Ser His Ser Glu
        355                 360                 365

Ser Leu Ile Arg Asn Ile Lys Glu Asn Glu Ser Thr Ser Arg Ser
    370                 375                 380

Asn Ser Leu Asp Ile Glu Arg Arg Leu His Tyr Tyr Met Ser Ser Ser
385                 390                 395                 400

Gly Leu Met Asn Gly Ile Ser Pro Ser Thr Ala Leu Pro Gln Thr Gln
                405                 410                 415

Ile Ser Ala Pro Leu Asp Leu Gly Gln Gln Ala Thr Leu Leu Ile Leu
            420                 425                 430

Gln Arg Ile Tyr Gln Glu Leu Lys Val Val Thr Lys Arg Met Met Glu
```

```
        435                 440                 445
Thr Asp Arg Glu Gly Gln Ala Ser Asn Asn Trp Lys Phe Ala Ala Met
            450                 455                 460

Val Val Asp Arg Leu Cys Leu Tyr Val Phe Thr Met Phe Ile Leu Ala
465                 470                 475                 480

Ser Thr Ile Gly Ile Phe Ser Ser Ala Pro Tyr Leu Val Ala
                485                 490
```

<210> SEQ ID NO 3
<211> LENGTH: 1104
<212> TYPE: DNA
<213> ORGANISM: Artificial Sequence
<220> FEATURE:
<223> OTHER INFORMATION: Human RIC3 (Accession number for Human RIC 3 sequence is NM_024557)

<400> SEQUENCE: 3

```
atggcgtact ccacagtgca gagagtcgct ctggcttctg gcttgtcct ggctctgtcg      60
ctgctgctgc ccaaggcctt cctgtcccgc gggaagcggc aggagccgcc gccgacacct    120
gaaggaaaat tgggccgatt tccacctatg atgcatcatc accaggcacc ctcagatggc    180
cagactcctg ggctcgtttt ccagaggtct caccttgccg aggcatttgc aaaggccaaa    240
ggatcaggtg gaggtgctgg aggaggaggt agtggaagag gtctgatggg cagattatt    300
ccaatctacg gttttgggat tttttttatat atactgtaca ttctatttaa gctctcaaag    360
gggaaaacaa ctgcagagga tgggaaatgc tatactgcca tgcctggaaa cacccacagg    420
aaaattacca gttttgagct tgctcaactg caagaaaaac tgaaggagac agaagcagcc    480
atggaaaaat taatcaacag agtgggacct aatggtgaga gagcacagac tgtgacttct    540
gaccaagaga aacggttgct acatcagctc cgagaaatca ccagggtcat gaagaagga    600
aaattcattg acagattttc tccagagaaa gaagctgagg aggcccctta catggaggac    660
tgggaaggtt accctgaaga gacttaccca atttatgacc tttcagactg tatcaagcgt    720
aggcaagaaa caatcttggt ggattaccct gacccaaaag aactttctgc tgaagaaata    780
gctgaaagaa tgggaatgat agaagaggaa gaatcagatc atttggggttg ggaaagtctg    840
cccactgacc ccagagccca ggaagataat tctgttacct cgtgtgatcc aaagccagaa    900
acatgttcct gctgttttca tgaagacgag atcctgctg tcttggcaga gaatgctgga    960
ttcagtgcag atagctaccc tgagcaagag gaaaccacca agaagagtg gtcccaagac    1020
tttaaagatg aagggttggg catcagcacc gataaagcat atacaggcag catgctgagg    1080
aagcgtaacc cccagggttt agag                                             1104
```

<210> SEQ ID NO 4
<211> LENGTH: 368
<212> TYPE: PRT
<213> ORGANISM: Artificial Sequence
<220> FEATURE:
<223> OTHER INFORMATION: Human RIC3 protein (translation of SEQ ID NO:3)

<400> SEQUENCE: 4

```
Met Ala Tyr Ser Thr Val Gln Arg Val Ala Leu Ala Ser Gly Leu Val
1               5                   10                  15

Leu Ala Leu Ser Leu Leu Leu Pro Lys Ala Phe Leu Ser Arg Gly Lys
                20                  25                  30

Arg Gln Glu Pro Pro Pro Thr Pro Glu Gly Lys Leu Gly Arg Phe Pro
            35                  40                  45
```

```
Pro Met Met His His His Gln Ala Pro Ser Asp Gly Gln Thr Pro Gly
    50                  55                  60

Ala Arg Phe Gln Arg Ser His Leu Ala Glu Ala Phe Ala Lys Ala Lys
65                  70                  75                  80

Gly Ser Gly Gly Gly Ala Gly Gly Gly Ser Gly Arg Gly Leu Met
                85                  90                  95

Gly Gln Ile Ile Pro Ile Tyr Gly Phe Gly Ile Phe Leu Tyr Ile Leu
                100                 105                 110

Tyr Ile Leu Phe Lys Leu Ser Lys Gly Lys Thr Thr Ala Glu Asp Gly
            115                 120                 125

Lys Cys Tyr Thr Ala Met Pro Gly Asn Thr His Arg Lys Ile Thr Ser
130                 135                 140

Phe Glu Leu Ala Gln Leu Gln Glu Lys Leu Lys Glu Thr Glu Ala Ala
145                 150                 155                 160

Met Glu Lys Leu Ile Asn Arg Val Gly Pro Asn Gly Glu Arg Ala Gln
                165                 170                 175

Thr Val Thr Ser Asp Gln Glu Lys Arg Leu Leu His Gln Leu Arg Glu
            180                 185                 190

Ile Thr Arg Val Met Lys Glu Gly Lys Phe Ile Asp Arg Phe Ser Pro
        195                 200                 205

Glu Lys Glu Ala Glu Glu Ala Pro Tyr Met Glu Asp Trp Glu Gly Tyr
210                 215                 220

Pro Glu Glu Thr Tyr Pro Ile Tyr Asp Leu Ser Asp Cys Ile Lys Arg
225                 230                 235                 240

Arg Gln Glu Thr Ile Leu Val Asp Tyr Pro Asp Pro Lys Glu Leu Ser
                245                 250                 255

Ala Glu Glu Ile Ala Glu Arg Met Gly Met Ile Glu Glu Glu Ser
            260                 265                 270

Asp His Leu Gly Trp Glu Ser Leu Pro Thr Asp Pro Arg Ala Gln Glu
        275                 280                 285

Asp Asn Ser Val Thr Ser Cys Asp Pro Lys Pro Glu Thr Cys Ser Cys
290                 295                 300

Cys Phe His Glu Asp Glu Asp Pro Ala Val Leu Ala Glu Asn Ala Gly
305                 310                 315                 320

Phe Ser Ala Asp Ser Tyr Pro Glu Gln Glu Glu Thr Thr Lys Glu Glu
                325                 330                 335

Trp Ser Gln Asp Phe Lys Asp Glu Gly Leu Gly Ile Ser Thr Asp Lys
            340                 345                 350

Ala Tyr Thr Gly Ser Met Leu Arg Lys Arg Asn Pro Gln Gly Leu Glu
        355                 360                 365
```

<210> SEQ ID NO 5
<211> LENGTH: 1095
<212> TYPE: DNA
<213> ORGANISM: Artificial Sequence
<220> FEATURE:
<223> OTHER INFORMATION: Hco RIC3 (predictive, in view of accession numbers HQ116824.1 and HQ116823.1)

<400> SEQUENCE: 5

```
atgcctgttc acgggcgaga gcgggaaaga aaacgtcggc gacgccgttc cgatagcgaa      60
gatgacgaca gcgttttcac aggatggaaa cttggtttgg ttgtgggtgt gattgtgatt     120
tgttttgcta tgctctatcc aacactaatt catccaatgc tgatgagcct attgggtcga     180
tcaccacctc cgccaccagc tgtcccttcg cgaccgccaa tcatcctgg aatgggtggt      240
```

```
cctggcggtg gccgacctgg tggtccgtca cggcatgatg ttcatcccgc tatgcggatg      300
gctcagcagc aggctgaaac gcaatcgagt gggcgaggat ctttcacatg gatgctaccc      360
ctgtacaccg tgggagtagt gatcttcctc ctatacactc tatttaagtc aaaaggcaag      420
aggaagagac gttctcgtta cgggtcatct gatgaaagct ctgatgatga cgacgtgtac      480
aacagccgac ttaaaaagaa aatcggcaaa cgaaaactcc gtagtctcca agaacgacta      540
caacagactg aagaggcgat gagcaagatc ttagagcaac tagaagctgt tcaagcagct      600
ggtgctcttg ttgaaggtga actgccgaag aaagatgtac cgggtgaagg caaagaagat      660
cagaaagcgg aaggtgcaaa tgaagtgaac ccgaaaaatg agcaatatat caacgattta      720
gaaaaggctc tcagagattt taagatctta tcggaagctt acgaagacga aagagcctc      780 cgtcgacatg gatcccattc tcaatcagag gaggatgaaa cgagctcaga agagttaaac      840
tcaggatcgg acgaagatga ggaggaaaac gaggaagaag agcaacccgt gaaggactcg      900
ggtagaaaga gaaaaggtc gaaagactct gaagaagacg ctgaggacgc ttcagaagag      960
gagctactga aggagaccaa aggcaaatcg gcaaaccaca acgtcaaaga gaacacgcca     1020
ccggctgagt ccacaattac atcaaaggaa tcggcaaaat catcaaaaca gtacgacga     1080 cgaccgaaaa aagtc                                                    1095
```

<210> SEQ ID NO 6
<211> LENGTH: 365
<212> TYPE: PRT
<213> ORGANISM: Artificial Sequence
<220> FEATURE:
<223> OTHER INFORMATION: Hco RIC3 protein - translation of SEQ ID NO: 5

<400> SEQUENCE: 6

```
Met Pro Val His Gly Arg Glu Arg Glu Arg Lys Arg Arg Arg Arg
 1               5                  10                  15

Ser Asp Ser Glu Asp Asp Ser Val Phe Thr Gly Trp Lys Leu Gly
                20                  25                  30

Leu Val Val Gly Val Ile Val Ile Cys Phe Ala Met Leu Tyr Pro Thr
                35                  40                  45

Leu Ile His Pro Met Leu Met Ser Leu Leu Gly Arg Ser Pro Pro Pro
        50                  55                  60

Pro Pro Ala Val Pro Ser Arg Pro Pro Ile His Pro Gly Met Gly Gly
65                      70                  75                  80

Pro Gly Gly Gly Arg Pro Gly Gly Pro Ser Arg His Asp Val His Pro
                        85                  90                  95

Ala Met Arg Met Ala Gln Gln Gln Ala Glu Thr Gln Ser Ser Gly Arg
                100                 105                 110

Gly Ser Phe Thr Trp Met Leu Pro Leu Tyr Thr Val Gly Val Val Ile
            115                 120                 125

Phe Leu Leu Tyr Thr Leu Phe Lys Ser Lys Gly Lys Arg Lys Arg Arg
    130                 135                 140

Ser Arg Tyr Gly Ser Ser Asp Glu Ser Ser Asp Asp Asp Val Tyr
145                 150                 155                 160

Asn Ser Arg Leu Lys Lys Lys Ile Gly Lys Arg Lys Leu Arg Ser Leu
                165                 170                 175

Gln Glu Arg Leu Gln Gln Thr Glu Glu Ala Met Ser Lys Ile Leu Glu
            180                 185                 190

Gln Leu Glu Ala Val Gln Ala Ala Gly Ala Leu Val Glu Gly Glu Leu
        195                 200                 205
```

Pro Lys Lys Asp Val Pro Gly Glu Gly Lys Glu Asp Gln Lys Ala Glu
    210                 215                 220

Gly Ala Asn Glu Val Asn Pro Lys Asn Glu Gln Tyr Ile Asn Asp Leu
225                 230                 235                 240

Glu Lys Ala Leu Arg Asp Phe Lys Ile Leu Ser Glu Ala Tyr Glu Asp
            245                 250                 255

Glu Lys Ser Leu Arg Arg His Gly Ser His Ser Gln Ser Glu Glu Asp
        260                 265                 270

Glu Thr Ser Ser Glu Glu Leu Asn Ser Gly Ser Asp Glu Asp Glu Glu
    275                 280                 285

Glu Asn Glu Glu Glu Gln Pro Val Lys Asp Ser Gly Arg Lys Lys
290                 295                 300

Lys Arg Ser Lys Asp Ser Glu Glu Asp Ala Glu Asp Ala Ser Glu Glu
305                 310                 315                 320

Glu Leu Leu Lys Glu Thr Lys Gly Lys Ser Ala Asn His Asn Val Lys
            325                 330                 335

Glu Asn Thr Pro Pro Ala Glu Ser Thr Ile Thr Ser Lys Glu Ser Ala
        340                 345                 350

Lys Ser Ser Lys Gln Val Arg Arg Pro Lys Lys Val
    355                 360                 365

<210> SEQ ID NO 7
<211> LENGTH: 1494
<212> TYPE: DNA
<213> ORGANISM: Artificial Sequence
<220> FEATURE:
<223> OTHER INFORMATION: Cel ACR-16 (Accession number for Caenorhabditis
      elegans ACR-16 sequence is NM_072806)

<400> SEQUENCE: 7
atgtctgtct gcacccttct catctcgtgc gcaattcttg cggcaccgac tctcggatca      60
ctgcaggagc gcagattgta tgaggatttg atgagaaatt ataacaatct ggaacgtcct     120
gttgcaaatc attccgagcc agttacagta catctaaagg tagccctcca acaaataatt     180
gacgtagacg agaaaaatca agtagtttat gtaaatgcat ggctggatta tacatggaac     240
gactataatt tggtttggga taaagctgaa tacggtaaca tcacagatgt ccgttttcca     300
gctggaaaga tctggaaacc agatgttcta ttatataaca gtgttgacac aaattttgat     360
tcaacgtatc aaaccaatat gattgtgtat tcaactggct ggtgcattg ggttccaccg      420 ggaatattta agatttcatg taaaattgat attcagtggt ttccatttga cgagcaaaaa     480 tgtttctttta aatttggttc atggactat gacggttata aacttgatct tcaaccagca     540
acgggtggat tgatatcag tgaatatatt tcaaacggag aatgggcttt acctttgaca      600
actgtggagc gaaacgaaaa gttttatgat tgctgtccgg aaccttatcc agatgttcat     660
ttttatcttc acatgagacg gcgaactctt tattacgggt tcaacttaat tatgccatgt     720
atattgacaa ctcttatgac acttctagga ttcacactc ctcctgatgc aggagagaaa      780
atcactcttc aaatcacggt cttactttca atttgcttct ttttgagtat tgtttcggag     840
atgtcacctc caacatcgga agctgttcct ttactaggta tattttttac gtgttgtatg     900
attgtggtta ctgcatcgac agtcttcacc gtctacgttc tcaacttaca ttaccgtact     960
ccggagaccc acgatatggg accatggaca cgtaacctcc ttctctattg gattccatgg    1020
attcttcgaa tgaaacgacc cggtcacaac ttgacatatg cttcacttcc atcattattt    1080
tccactaagc caatcgtca ctcggaatca ttgatccgta acatcaaaga caatgaacat    1140

```
tcactttcac gagcaaactc atttgatgcc gattgtcgat tgaatcaata tattatgaca    1200
caatctgtta gtaatgggtt gacaagtctt ggcagtattc aagtacaat gatttcatca     1260 aatggtacaa ctacagacgt ctcacaacag gcgacacttc tgattcttca cagaatatac    1320
catgaattga agattgttac gaagagaatg atagaaggtg ataaggaaga acaggcatgc    1380
aataattgga aatttgcggc catggttgtg gaccgccttt gtttatacgt cttcacaata    1440
ttcataattg tttcaacgat tggaattttc tggtcagcac cgtatcttgt cgcc          1494
```

<210> SEQ ID NO 8
<211> LENGTH: 498
<212> TYPE: PRT
<213> ORGANISM: Artificial Sequence
<220> FEATURE:
<223> OTHER INFORMATION: Cel ACR-16 protein
      (gi|17557182|ref|NP_505207.1| Protein ACR-16, isoform a
      Caenorhabditis elegans)

<400> SEQUENCE: 8

```
Met Ser Val Cys Thr Leu Leu Ile Ser Cys Ala Ile Leu Ala Ala Pro
1               5                   10                  15

Thr Leu Gly Ser Leu Gln Glu Arg Arg Leu Tyr Glu Asp Leu Met Arg
            20                  25                  30

Asn Tyr Asn Asn Leu Glu Arg Pro Val Ala Asn His Ser Glu Pro Val
        35                  40                  45

Thr Val His Leu Lys Val Ala Leu Gln Gln Ile Ile Asp Val Asp Glu
    50                  55                  60

Lys Asn Gln Val Val Tyr Val Asn Ala Trp Leu Asp Tyr Thr Trp Asn
65                  70                  75                  80

Asp Tyr Asn Leu Val Trp Asp Lys Ala Glu Tyr Gly Asn Ile Thr Asp
                85                  90                  95

Val Arg Phe Pro Ala Gly Lys Ile Trp Lys Pro Asp Val Leu Leu Tyr
            100                 105                 110

Asn Ser Val Asp Thr Asn Phe Asp Ser Thr Tyr Gln Thr Asn Met Ile
        115                 120                 125

Val Tyr Ser Thr Gly Leu Val His Trp Val Pro Pro Gly Ile Phe Lys
    130                 135                 140

Ile Ser Cys Lys Ile Asp Ile Gln Trp Phe Pro Phe Asp Glu Gln Lys
145                 150                 155                 160

Cys Phe Phe Lys Phe Gly Ser Trp Thr Tyr Asp Gly Tyr Lys Leu Asp
                165                 170                 175

Leu Gln Pro Ala Thr Gly Gly Phe Asp Ile Ser Glu Tyr Ile Ser Asn
            180                 185                 190

Gly Glu Trp Ala Leu Pro Leu Thr Thr Val Glu Arg Asn Glu Lys Phe
        195                 200                 205

Tyr Asp Cys Cys Pro Glu Pro Tyr Pro Asp Val His Phe Tyr Leu His
    210                 215                 220

Met Arg Arg Arg Thr Leu Tyr Tyr Gly Phe Asn Leu Ile Met Pro Cys
225                 230                 235                 240

Ile Leu Thr Thr Leu Met Thr Leu Leu Gly Phe Thr Leu Pro Pro Asp
                245                 250                 255

Ala Gly Glu Lys Ile Thr Leu Gln Ile Thr Val Leu Leu Ser Ile Cys
            260                 265                 270

Phe Phe Leu Ser Ile Val Ser Glu Met Ser Pro Pro Thr Ser Glu Ala
        275                 280                 285

Val Pro Leu Leu Gly Ile Phe Phe Thr Cys Cys Met Ile Val Val Thr
```

```
                290               295              300
Ala Ser Thr Val Phe Thr Val Tyr Val Leu Asn Leu His Tyr Arg Thr
305                 310              315              320

Pro Glu Thr His Asp Met Gly Pro Trp Thr Arg Asn Leu Leu Leu Tyr
                325              330              335

Trp Ile Pro Trp Ile Leu Arg Met Lys Arg Pro Gly His Asn Leu Thr
            340              345              350

Tyr Ala Ser Leu Pro Ser Leu Phe Ser Thr Lys Pro Asn Arg His Ser
        355              360              365

Glu Ser Leu Ile Arg Asn Ile Lys Asp Asn Glu His Ser Leu Ser Arg
    370              375              380

Ala Asn Ser Phe Asp Ala Asp Cys Arg Leu Asn Gln Tyr Ile Met Thr
385              390              395              400

Gln Ser Val Ser Asn Gly Leu Thr Ser Leu Gly Ser Ile Pro Ser Thr
                405              410              415

Met Ile Ser Ser Asn Gly Thr Thr Thr Asp Val Ser Gln Gln Ala Thr
            420              425              430

Leu Leu Ile Leu His Arg Ile Tyr His Glu Leu Lys Ile Val Thr Lys
        435              440              445

Arg Met Ile Glu Gly Asp Lys Glu Glu Gln Ala Cys Asn Asn Trp Lys
    450              455              460

Phe Ala Ala Met Val Val Asp Arg Leu Cys Leu Tyr Val Phe Thr Ile
465              470              475              480

Phe Ile Ile Val Ser Thr Ile Gly Ile Phe Trp Ser Ala Pro Tyr Leu
                485              490              495

Val Ala
```

<210> SEQ ID NO 9
<211> LENGTH: 1134
<212> TYPE: DNA
<213> ORGANISM: Artificial Sequence
<220> FEATURE:
<223> OTHER INFORMATION: Cel Ric3 (Accession number for C. elegans RIC3 sequence is NM_068898.4)

<400> SEQUENCE: 9

```
atgccaaaaa ctgaacggcg tcgtgataga gatcgagaca gagatcgaga aggagaaac      60
agacgaaaaa gggatgatag ttacgatgat tacgatgaag aaggtggaat atcaggatgg    120
aagcttggtt tagtatttgg agtaatcgtt gtttgctttg caatgcttta tccaacactt    180
ttccatccaa tgctaatggg attcttgggt cgttcaccac catcaagtcc atcaataaac    240
caacaacgtc caccaattca tccagcaatg ggtgggggaa gtggacaacg tcatccaggt    300
ggtggtgcag atgtacatcc agcaatgaga atggctcaag cacaagctga agtcaatct    360
ggtggatcaa agggaatgtt cacatggatg ttacctgtat atacaatcgg agttgtttta    420
tttcttttgt atacgctgtt taaatcaaaa ggaaagaaat caaagcgaaa gaagagaaat    480
tattttgatt ctgaagacga tgatgatgaa tctgaaagtg agactaaata tggcggaaaa    540
tttggtaaaa agaagcttga aggacttcag aaaaggcttc gagagactga agtgcaatg    600
tctaagattt tagaacaact tgaatcagta caagctggcg ctaatcctgt cgacttagat    660
gctgccgata gaggtcgga caacttgaa gaagatccat cagttaaaga gcagttgga      720
ttaactgaaa ccaatgaaca atacataaaa gatcttgagg ttgcactgaa agagtttcag    780
tccttgtcaa aagaatatga taagcgaaa atgaagaaac tgaaaagaaa agattcttcg    840
```

-continued

```
agtgacgaag atgaagaaga cgaagaagag aatagctctg aattgtcaga aatcgaagag    900
gaagaagagg aagttaaacc agtgaaaaag tcaaaatcat cctcccaatc agttggaaaa    960
aggaagaatc gaccaaaaag cacatcagaa gaagaagatg aaggagaaga agaatcacga   1020
aaagttgcag aagatgctga agaagaagga attgacattg attctgagat ccgagagcac   1080
gcggaaaagg agaaaaaaga taaaaatgtg cgaaggcgga gacctaaaaa gact         1134
```

<210> SEQ ID NO 10
<211> LENGTH: 378
<212> TYPE: PRT
<213> ORGANISM: Artificial Sequence
<220> FEATURE:
<223> OTHER INFORMATION: Cel Ric3 protein (translation of SEQ ID NO:9)

<400> SEQUENCE: 10

```
Met Pro Lys Thr Glu Arg Arg Asp Arg Asp Arg Asp Arg Asp Arg
1               5                   10                  15

Glu Arg Arg Asn Arg Arg Lys Arg Asp Asp Ser Tyr Asp Asp Tyr Asp
            20                  25                  30

Glu Glu Gly Gly Ile Ser Gly Trp Lys Leu Gly Leu Val Phe Gly Val
        35                  40                  45

Ile Val Val Cys Phe Ala Met Leu Tyr Pro Thr Leu Phe His Pro Met
50                  55                  60

Leu Met Gly Phe Leu Gly Arg Ser Pro Pro Ser Ser Pro Ser Ile Asn
65                  70                  75                  80

Gln Gln Arg Pro Pro Ile His Pro Ala Met Gly Gly Ser Gly Gln
            85                  90                  95

Arg His Pro Gly Gly Gly Ala Asp Val His Pro Ala Met Arg Met Ala
        100                 105                 110

Gln Ala Gln Ala Glu Ser Gln Ser Gly Gly Ser Lys Gly Met Phe Thr
    115                 120                 125

Trp Met Leu Pro Val Tyr Thr Ile Gly Val Val Leu Phe Leu Leu Tyr
130                 135                 140

Thr Leu Phe Lys Ser Lys Gly Lys Lys Ser Lys Arg Lys Lys Arg Asn
145                 150                 155                 160

Tyr Phe Asp Ser Glu Asp Asp Asp Glu Ser Glu Ser Glu Thr Lys
                165                 170                 175

Tyr Gly Gly Lys Phe Gly Lys Lys Lys Leu Glu Gly Leu Gln Lys Arg
            180                 185                 190

Leu Arg Glu Thr Glu Ser Ala Met Ser Lys Ile Leu Glu Gln Leu Glu
        195                 200                 205

Ser Val Gln Ala Gly Ala Asn Pro Val Asp Leu Asp Ala Ala Asp Lys
    210                 215                 220

Arg Ser Glu Gln Leu Glu Asp Pro Ser Val Lys Glu Ala Val Gly
225                 230                 235                 240

Leu Thr Glu Thr Asn Glu Gln Tyr Ile Lys Asp Leu Glu Val Ala Leu
                245                 250                 255

Lys Glu Phe Gln Ser Leu Ser Lys Glu Tyr Asp Lys Ala Lys Met Lys
            260                 265                 270

Lys Leu Lys Arg Lys Asp Ser Ser Asp Glu Asp Glu Glu Asp Glu
        275                 280                 285

Glu Glu Asn Ser Ser Glu Leu Ser Glu Ile Glu Glu Glu Glu Glu
    290                 295                 300

Val Lys Pro Val Lys Lys Ser Lys Ser Ser Ser Gln Ser Val Gly Lys
305                 310                 315                 320
```

Arg Lys Asn Arg Pro Lys Ser Thr Ser Glu Glu Asp Glu Gly Glu
            325                 330                 335

Glu Glu Ser Arg Lys Val Ala Glu Asp Ala Glu Glu Gly Ile Asp
            340                 345                 350

Ile Asp Ser Glu Ile Arg Glu His Ala Glu Lys Glu Lys Asp Lys
            355                 360                 365

Asn Val Arg Arg Arg Arg Pro Lys Lys Thr
            370                 375

<210> SEQ ID NO 11
<211> LENGTH: 1521
<212> TYPE: DNA
<213> ORGANISM: Artificial Sequence
<220> FEATURE:
<223> OTHER INFORMATION: Dim ACR-16 (Dirofilaria immitis ACR-16
      sequence, sequence from clone 4346-2)

<400> SEQUENCE: 11
atgttactat cgtggatagt taattcattg gtacgatgcc tatttatgat tacattattt       60
gcatttctac aaattattac cggtagctat catgaacgtc gtctttatga tgatttaatg      120
aaaaattata ataatttgga acgtccggta caaaatcatt cggaacctgt cgtagtttat      180
ttaaaagtat cattgcaaca aattattgat gttgatgaga agaatcaaat tgtttatgta      240
aatgcatggc tcgattttgc atggaatgat tataaactta gatgggacaa aactaaatac      300
ggaaatataa cggatgttcg ttttccagct ggtaaaattt ggaaaccaga tgttctactt      360
tataatagcg tagatgcaaa ttttgattcg acctatccaa cgaatatgat tgtttataat      420
acaggtgata tatcatggat tccacctgct attttttaaaa ttagttgcaa aattaatatc      480
gaatggtttc cattcgatga acaacgttgt tttttttaagt ttggttcatg acatatgat       540 ggtgataaat tagatttaca acctggaaag ggtggttttg atatttcaga atatatgcca      600
agtggtgaat gggctttacc catgactacc gtatcaagaa cggtaaaatt ttatgaatgt      660
tgcccagaac catatcctga cctcaaattt tatttacatt taagacgtcg tacattatac      720
tatggtttca atttaataat gccttgtata ttaacaacaa tgatgacatt acttggtttt      780
acattaccac ctgatgctgg tgaaaagatt accctacaga taacagtgct cttatcaatc      840
tgtttctttc ttagcgttgt atccgaaatg tcaccaccaa cctcagaagc agtgccactt      900
ttaggaatat ttttttcttg ttgtatgatt gttgttaccg catcaacagt ttttacagta      960
tatgttttaa atttacatta tcgtacatct gaaacacatg aaatgggtac tttgacgaaa     1020
acattgctac tttattggct accgtatttg cttcgaataa atcggccagg cgttaattta     1080
tcatggaaag cattaccatc attatttcca tttacaaaac ccaggacaac gcatagcgaa     1140
tcactcatac gaaatattaa agaagctgaa tcaagcacaa ggtcaaattc attagatgtt     1200
gaatgtaggg tatgccaata tatgggtggt atttcaaatg gcaaaagtcc tatttcaacg     1260
gtaattaatg gacctatatt aaggcaaaca aattcatgcg ttgatattgg ccaacaagct     1320
actttgctca ttttgcaacg aatttatcaa gaacttaaga caataactaa acgtatgatg     1380
gatgcagaaa aggatgatgc aaaagcaaat aattggaaat tgcagcaat  tgttgttgat     1440 cgtttatgtt tatatatttt tacaatattt ataattgctt catcatgtgg tatattactt     1500
tcagcaccat attttattgc t                                              1521

<210> SEQ ID NO 12
<211> LENGTH: 1521

<212> TYPE: DNA
<213> ORGANISM: Artificial Sequence
<220> FEATURE:
<223> OTHER INFORMATION: Dim ACR-16 codon-optimized for expression in
      mammalian cells

<400> SEQUENCE: 12

```
atgctgctga gctggatcgt gaacagcctc gtgcggtgcc tgttcatgat acccctgttc      60
gccttcctgc agatcatcac cggatcctac cacgagcggc ggctgtacga cgacctgatg     120
aagaactaca caacctgga acggcccgtg cagaaccaca gcgagcctgt ggtggtgtac     180
ctgaaggtgt ccctgcagca gatcattgac gtggacgaga gaaccagat cgtgtacgtg     240
aacgcctggc tggacttcgc ctggaacgac tacaagctga tgggacaa gaccaaatac      300
ggcaacatca ccgacgtgcg gttccctgcc ggcaagatct ggaagcccga cgtgctgctg     360
tacaacagcg tggacgccaa cttcgacagc acctacccca ccaacatgat cgtgtataac     420
accggcgaca tcagctggat ccccctgcc atcttcaaga tcagctgcaa gatcaatatc      480
gagtggttcc cattcgacga gcagcggtgc ttcttcaagt tcggcagctg gacctacgac     540
ggcgataagc tggatctgca gcctggcaag ggcggcttcg acatctccga gtacatgccc     600
tctggcgagt gggccctgcc tatgaccacc gtgtcccgga ccgtgaagtt ctacgagtgc     660
tgccccgagc cctaccccga cctgaagttt tacctgcacc tgaggcggcg accctgtac      720
tacggcttca acctgatcat gcccgcatc ctgaccacca tgatgaccct gctgggcttc     780
accctgcctc agatgccgg cgagaagatc accctgcaga ttacagtgct gctgtctatc     840
tgcttcttcc tgtccgtggt gtccgagatg agcccccta catctgaggc cgtgcctctg     900
ctgggcatct tcttcagctg ctgtatgatc gtcgtgaccg ccagcaccgt gttcacagtg     960
tacgtgctga acctgcacta ccggaccagc gagacacacg agatgggcac cctgaccaag    1020
accctgctgc tgtattggct gccctacctg ctgcggatca cagaccccgg cgtgaacctg    1080
tcctggaagg ccctgccaag cctgttcccc ttcaccaaac ctcggaccac ccactccgag    1140
agcctgatcc ggaacatcaa agaggccgag agcagcaccc ggtccaactc cctggacgtg    1200
gaatgcagag tgtgccagta catgggcggc atcagcaacg gcaagagccc catctccacc    1260
gtgatcaacg cccccatcct gcggcagacc aacagctgtg tggacatcgg ccagcaggcc    1320
accctgctga tcctgcagag aatctaccag gaactgaaaa ccatcaccaa gcggatgatg    1380
gacgccgaga aggacgacgc caaggccaac aactggaagt cgccgccat cgtggtggac    1440
cggctgtgcc tgtacatctt caccatcttc atcattgcct ccagctgcgg catcctgctg    1500
tccgccccctt actttatcgc c                                              1521
```

<210> SEQ ID NO 13
<211> LENGTH: 507
<212> TYPE: PRT
<213> ORGANISM: Artificial Sequence
<220> FEATURE:
<223> OTHER INFORMATION: Dim ACR-16 (translation of SEQ ID NOs:11 & 12)

<400> SEQUENCE: 13

Met Leu Leu Ser Trp Ile Val Asn Ser Leu Val Arg Cys Leu Phe Met
1               5                   10                  15

Ile Thr Leu Phe Ala Phe Leu Gln Ile Ile Thr Gly Ser Tyr His Glu
            20                  25                  30

Arg Arg Leu Tyr Asp Asp Leu Met Lys Asn Tyr Asn Asn Leu Glu Arg
        35                  40                  45

-continued

```
Pro Val Gln Asn His Ser Glu Pro Val Val Tyr Leu Lys Val Ser
    50                  55                  60
Leu Gln Gln Ile Ile Asp Val Asp Glu Lys Asn Gln Ile Val Tyr Val
65                  70                  75                  80
Asn Ala Trp Leu Asp Phe Ala Trp Asn Asp Tyr Lys Leu Arg Trp Asp
                85                  90                  95
Lys Thr Lys Tyr Gly Asn Ile Thr Asp Val Arg Phe Pro Ala Gly Lys
            100                 105                 110
Ile Trp Lys Pro Asp Val Leu Leu Tyr Asn Ser Val Asp Ala Asn Phe
        115                 120                 125
Asp Ser Thr Tyr Pro Thr Asn Met Ile Val Tyr Asn Thr Gly Asp Ile
    130                 135                 140
Ser Trp Ile Pro Pro Ala Ile Phe Lys Ile Ser Cys Lys Ile Asn Ile
145                 150                 155                 160
Glu Trp Phe Pro Phe Asp Glu Gln Arg Cys Phe Phe Lys Phe Gly Ser
                165                 170                 175
Trp Thr Tyr Asp Gly Asp Lys Leu Asp Leu Gln Pro Gly Lys Gly Gly
            180                 185                 190
Phe Asp Ile Ser Glu Tyr Met Pro Ser Gly Glu Trp Ala Leu Pro Met
        195                 200                 205
Thr Thr Val Ser Arg Thr Val Lys Phe Tyr Glu Cys Cys Pro Glu Pro
    210                 215                 220
Tyr Pro Asp Leu Lys Phe Tyr Leu His Leu Arg Arg Thr Leu Tyr
225                 230                 235                 240
Tyr Gly Phe Asn Leu Ile Met Pro Cys Ile Leu Thr Thr Met Met Thr
                245                 250                 255
Leu Leu Gly Phe Thr Leu Pro Pro Asp Ala Gly Glu Lys Ile Thr Leu
            260                 265                 270
Gln Ile Thr Val Leu Leu Ser Ile Cys Phe Phe Leu Ser Val Val Ser
        275                 280                 285
Glu Met Ser Pro Pro Thr Ser Glu Ala Val Pro Leu Leu Gly Ile Phe
    290                 295                 300
Phe Ser Cys Cys Met Ile Val Val Thr Ala Ser Thr Val Phe Thr Val
305                 310                 315                 320
Tyr Val Leu Asn Leu His Tyr Arg Thr Ser Glu Thr His Glu Met Gly
                325                 330                 335
Thr Leu Thr Lys Thr Leu Leu Leu Tyr Trp Leu Pro Tyr Leu Leu Arg
            340                 345                 350
Ile Asn Arg Pro Gly Val Asn Leu Ser Trp Lys Ala Leu Pro Ser Leu
        355                 360                 365
Phe Pro Phe Thr Lys Pro Arg Thr Thr His Ser Glu Ser Leu Ile Arg
    370                 375                 380
Asn Ile Lys Glu Ala Glu Ser Ser Thr Arg Ser Asn Ser Leu Asp Val
385                 390                 395                 400
Glu Cys Arg Val Cys Gln Tyr Met Gly Gly Ile Ser Asn Gly Lys Ser
                405                 410                 415
Pro Ile Ser Thr Val Ile Asn Gly Pro Ile Leu Arg Gln Thr Asn Ser
            420                 425                 430
Cys Val Asp Ile Gly Gln Gln Ala Thr Leu Leu Ile Leu Gln Arg Ile
        435                 440                 445
Tyr Gln Glu Leu Lys Thr Ile Thr Lys Arg Met Met Asp Ala Glu Lys
    450                 455                 460
Asp Asp Ala Lys Ala Asn Asn Trp Lys Phe Ala Ala Ile Val Val Asp
```

```
                465                 470                 475                 480
Arg Leu Cys Leu Tyr Ile Phe Thr Ile Phe Ile Ile Ala Ser Ser Cys
                    485                 490                 495

Gly Ile Leu Leu Ser Ala Pro Tyr Phe Ile Ala
                500                 505

<210> SEQ ID NO 14
<211> LENGTH: 891
<212> TYPE: DNA
<213> ORGANISM: Artificial Sequence
<220> FEATURE:
<223> OTHER INFORMATION: Dim RIC3 short sequence from clone 4350-1

<400> SEQUENCE: 14
atgtcagccg aagcatcatc gtatcactct agaaggcgac gacgaactta ttcagaagaa    60
gagtcaccac tttcaggatg aagcttgga attgttattg gagtgataat catgtgtttt   120
gcaatgcttt atccgaacat gcttcatcca ttagtatctt cattttccg tgctccacct   180 acacgaaaaa cagttaccaa tcgaccaccg atccatccag cgatgaattc accacgatct   240
cgtcctgatt tacatccagg tatgcgaatg gcggcagcaa gtcaaccaga tgtaactaca   300
ccatcttcct catccaaagg aatttttgca tggatgcttc aatttatac agttggtgtc    360 gttgcattcc ttatttatac cttaattaag tcaagaaga aacgacgaag taggcgacat    420
gattattcat cgacggaaag tgaatcagat gaagattata atcgtaatga tgggcgtact   480
ggcagcatcg gtaaacgaaa attaaaagga cttcaggaac gtttaaggca aactgaaatg   540
gcgatggaaa agattttgga acagctgaat acaattctg ctgaggcaac taatgtaacg    600
aaacaaaatt taacaaaaaa aaccgataat atgaaaacag tgaatcagcg tcttgaccaa   660
caagatggga aaacagagca atatttgcgg gatcttgaag aagcattacg cgatttcaag   720
gagctatcca aaaaatacgg aaaagaagaa gaggatgaaa gtaataccag tgatgctgag   780
ccatatactg atgaaagttt acacgatgaa atcgtcatgg acgcaagtaa tcagtacaaa   840
ctccagaaat tcaatccttc agatgaacat ctaagaaagc gtagaaaaag c            891

<210> SEQ ID NO 15
<211> LENGTH: 891
<212> TYPE: DNA
<213> ORGANISM: Artificial Sequence
<220> FEATURE:
<223> OTHER INFORMATION: Dim RIC3 codon-optimized for expression in
      mammalian cells

<400> SEQUENCE: 15
atgagcgccg aggccagcag ctaccacagc ggcggagaa aagaaccta cagcgaggaa      60 gagagccccc tgagcggctg aagctgggc atcgtgatcg gcgtgatcat catgtgcttc   120
gccatgctgt accccaacat gctgcacccc ctggtgtcca gcttcttcag agcccccct    180 accagaaaga ccgtgaccaa cagacccccc atccaccccg ccatgaacag ccccagaagc   240
agacccgatc tgcaccccgg catgagaatg gccgctgcct ctcagcctga cgtgaccaca   300
cctagcagca gctccaaggg catcttcgcc tggatgctgc ccatctacac cgtgggcgtg   360
gtggccttcc tgatctacac cctgatcaag agcaagaaga gcggcgagag cagacggcac   420
gactacagca gcacagagag cgagagcgac gaggactaca accggaacga cggcagaacc   480
ggcagcatcg gcaagcggaa gctgaagggc ctgcaggaac ggctgagaca gaccgagatg   540
gctatggaaa agatcctgga acagctgaac accatcagcg ccgaagccac caacgtgaca   600
```

```
aagcagaacc tgaccaagaa aaccgacaac atgaagacag tgaaccagag gctggaccag    660
caggacggca agaccgagca gtacctgcgg gatctggaag aggccctgcg ggacttcaaa    720
gagctgtcca agaagtacgg caaagaggaa gaggacgagt ccaacaccag cgacgccgag    780
ccctacaccg atgagagcct gcacgacgag atcgtgatgg acgccagcaa ccagtacaag    840
ctgcagaaat tcaacccctc cgacgagcac ctgagaaagc ggagaaagag c            891
```

```
<210> SEQ ID NO 16
<211> LENGTH: 297
<212> TYPE: PRT
<213> ORGANISM: Artificial Sequence
<220> FEATURE:
<223> OTHER INFORMATION: Dim Ric3 (translation of SEQ ID NOs:14 & 15)

<400> SEQUENCE: 16
```

Met Ser Ala Glu Ala Ser Ser Tyr His Ser Arg Arg Arg Arg Thr
1               5                   10                  15

Tyr Ser Glu Glu Glu Ser Pro Leu Ser Gly Trp Lys Leu Gly Ile Val
            20                  25                  30

Ile Gly Val Ile Ile Met Cys Phe Ala Met Leu Tyr Pro Asn Met Leu
        35                  40                  45

His Pro Leu Val Ser Ser Phe Phe Arg Ala Pro Pro Thr Arg Lys Thr
    50                  55                  60

Val Thr Asn Arg Pro Pro Ile His Pro Ala Met Asn Ser Pro Arg Ser
65                  70                  75                  80

Arg Pro Asp Leu His Pro Gly Met Arg Met Ala Ala Ala Ser Gln Pro
                85                  90                  95

Asp Val Thr Thr Pro Ser Ser Ser Lys Gly Ile Phe Ala Trp Met
            100                 105                 110

Leu Pro Ile Tyr Thr Val Gly Val Val Ala Phe Leu Ile Tyr Thr Leu
        115                 120                 125

Ile Lys Ser Lys Lys Lys Arg Arg Ser Arg Arg His Asp Tyr Ser Ser
    130                 135                 140

Thr Glu Ser Glu Ser Asp Glu Asp Tyr Asn Arg Asn Asp Gly Arg Thr
145                 150                 155                 160

Gly Ser Ile Gly Lys Arg Lys Leu Lys Gly Leu Gln Glu Arg Leu Arg
                165                 170                 175

Gln Thr Glu Met Ala Met Glu Lys Ile Leu Glu Gln Leu Asn Thr Ile
            180                 185                 190

Ser Ala Glu Ala Thr Asn Val Thr Lys Gln Asn Leu Thr Lys Lys Thr
        195                 200                 205

Asp Asn Met Lys Thr Val Asn Gln Arg Leu Asp Gln Asp Gly Lys
    210                 215                 220

Thr Glu Gln Tyr Leu Arg Asp Leu Glu Glu Ala Leu Arg Asp Phe Lys
225                 230                 235                 240

Glu Leu Ser Lys Lys Tyr Gly Lys Glu Glu Asp Glu Ser Asn Thr
                245                 250                 255

Ser Asp Ala Glu Pro Tyr Thr Asp Glu Ser Leu His Asp Glu Ile Val
            260                 265                 270

Met Asp Ala Ser Asn Gln Tyr Lys Leu Gln Lys Phe Asn Pro Ser Asp
        275                 280                 285

Glu His Leu Arg Lys Arg Lys Ser
    290                 295

<210> SEQ ID NO 17

```
<211> LENGTH: 42
<212> TYPE: DNA
<213> ORGANISM: Artificial Sequence
<220> FEATURE:
<223> OTHER INFORMATION: 9924-01 forward primer PmlI InFusion

<400> SEQUENCE: 17
aggtgtcgtg aacacgtgcc accatgtgga gcttgctgat cg                              42

<210> SEQ ID NO 18
<211> LENGTH: 38
<212> TYPE: DNA
<213> ORGANISM: Artificial Sequence
<220> FEATURE:
<223> OTHER INFORMATION: 9924-02 reverse primer PmlI InFusion

<400> SEQUENCE: 18
agcggccgcg accacgtgct aggcgaccag atatggag                                  38

<210> SEQ ID NO 19
<211> LENGTH: 494
<212> TYPE: PRT
<213> ORGANISM: Artificial Sequence
<220> FEATURE:
<223> OTHER INFORMATION: CDJ95690 Neurotransmitter-gated ion-channel
      transmembrane region domain containing protein [Haemonchus
      contortus]

<400> SEQUENCE: 19
```

Met Trp Ser Leu Leu Ile Ala Cys Ser Phe Val Ala Val Ala Val Val
1               5                   10                  15

Ile Ala Ser Tyr Asp Glu Arg Arg Leu Tyr Glu Asp Leu Met Arg Asp
                20                  25                  30

Tyr Asn Ser Leu Glu Arg Pro Val Ala Asn His Ser Lys Pro Val Thr
            35                  40                  45

Val Tyr Leu Lys Val Ser Leu Gln Gln Ile Ile Asp Val Asp Glu Lys
        50                  55                  60

Asn Gln Ile Val Tyr Val Asn Ala Trp Leu Asp Tyr Thr Trp Lys Asp
65                  70                  75                  80

Tyr Lys Leu Val Trp Asp Val Ser Glu Tyr Gly Asn Ile Thr Asp Val
                85                  90                  95

Arg Phe Pro Ala Gly Arg Ile Trp Lys Pro Asp Val Leu Leu Tyr Asn
            100                 105                 110

Ser Val Asp Thr Asn Phe Asp Ser Thr Tyr Pro Thr Asn Met Val Val
        115                 120                 125

Tyr Ser Thr Gly Asp Val His Trp Val Pro Pro Gly Ile Phe Lys Ile
    130                 135                 140

Ser Cys Lys Ile Asp Ile Glu Trp Phe Pro Phe Asp Glu Gln Arg Cys
145                 150                 155                 160

Lys Phe Lys Phe Gly Ser Trp Thr Tyr Asp Gly Phe Lys Leu Asp Leu
                165                 170                 175

Gln Pro Ala Lys Lys Gly Phe Asp Ile Ser Glu Tyr Leu Pro Asn Gly
            180                 185                 190

Glu Trp Thr Leu Pro Leu Thr Thr Val Ser Arg Asn Val Lys Phe Tyr
        195                 200                 205

Asp Cys Cys Pro Glu Pro Tyr Pro Asp Leu Thr Phe Tyr Leu His Met
    210                 215                 220

Arg Arg Arg Thr Leu Tyr Tyr Gly Phe Asn Leu Ile Met Pro Cys Ile
225                 230                 235                 240

```
Leu Thr Thr Leu Met Thr Leu Leu Gly Phe Thr Leu Pro Pro Asp Ala
                245                 250                 255

Gly Glu Lys Ile Thr Leu Gln Ile Thr Val Leu Leu Ser Ile Cys Phe
            260                 265                 270

Phe Leu Ser Ile Val Ser Glu Met Ser Pro Pro Thr Ser Glu Ala Val
        275                 280                 285

Pro Leu Leu Gly Ile Phe Phe Thr Cys Cys Met Ile Val Thr Ala
    290                 295                 300

Ser Thr Val Phe Thr Val Tyr Val Leu Asn Leu His Tyr Arg Thr Pro
305                 310                 315                 320

Glu Thr His Glu Met Thr Pro Val Met Arg Ser Val Leu Leu Tyr Trp
                325                 330                 335

Leu Pro Trp Met Leu Arg Met Lys Arg Pro Gly Val Lys Leu Thr Tyr
            340                 345                 350

Ala Thr Leu Pro Ser Leu Phe Asn Leu Lys Leu Lys Ser His Ser Glu
        355                 360                 365

Ser Leu Ile Arg Asn Ile Lys Glu Asn Glu Ser Ser Thr Ser Arg Ser
    370                 375                 380

Asn Ser Leu Asp Ile Glu Arg Arg Leu His Tyr Tyr Met Ser Ser Ser
385                 390                 395                 400

Gly Leu Met Asn Gly Ile Ser Pro Ser Thr Ala Leu Pro Gln Thr Gln
                405                 410                 415

Ile Ser Ala Pro Leu Asp Leu Gly Gln Ala Thr Leu Leu Ile Leu
            420                 425                 430

Gln Arg Ile Tyr Gln Glu Leu Lys Val Val Thr Lys Arg Met Met Glu
        435                 440                 445

Thr Asp Arg Glu Gly Gln Ala Ser Asn Asn Trp Lys Phe Ala Ala Met
    450                 455                 460

Val Val Asp Arg Leu Cys Leu Tyr Val Phe Thr Met Phe Ile Leu Ala
465                 470                 475                 480

Ser Thr Ile Gly Ile Phe Ser Ser Ala Pro Tyr Leu Val Ala
                485                 490

<210> SEQ ID NO 20
<211> LENGTH: 500
<212> TYPE: PRT
<213> ORGANISM: Artificial Sequence
<220> FEATURE:
<223> OTHER INFORMATION: XP_003110639 CRE-ACR-16 protein [Caenorhabditis
      remanei]

<400> SEQUENCE: 20

Met Ser Val Cys Ala Leu Leu Ser Cys Ala Ile Phe Cys Ala Thr
1               5                   10                  15

Pro Ala Phe Gly Ser Leu Gln Glu Arg Arg Leu Tyr Glu Asp Leu Met
            20                  25                  30

Arg Asn Tyr Asn Asn Leu Glu Arg Pro Val Ala Asn His Ser Glu Pro
        35                  40                  45

Val Thr Val His Leu Lys Val Ala Leu Gln Gln Ile Ile Asp Val Asp
    50                  55                  60

Glu Lys Asn Gln Val Val Tyr Val Asn Ala Trp Leu Asp Tyr Thr Trp
65                  70                  75                  80

Lys Asp Tyr Asn Leu Val Trp Asp Gln Ala Glu Tyr Gly Asn Ile Thr
                85                  90                  95

Asp Val Arg Phe Pro Ala Gly Lys Ile Trp Lys Pro Asp Val Leu Leu
            100                 105                 110
```

Tyr Asn Ser Val Asp Thr Asn Phe Asp Ser Thr Tyr Gln Thr Asn Met
            115                 120                 125

Ile Val Tyr Ser Ser Gly Leu Val His Trp Val Pro Pro Gly Ile Phe
130                 135                 140

Lys Ile Ser Cys Lys Ile Asp Ile Gln Trp Phe Pro Phe Asp Glu Gln
145                 150                 155                 160

Lys Cys Phe Phe Lys Phe Gly Ser Trp Thr Tyr Asp Gly Tyr Lys Leu
                165                 170                 175

Asp Leu Gln Pro Ala Thr Gly Gly Phe Asp Ile Ser Glu Tyr Leu Pro
            180                 185                 190

Asn Gly Glu Trp Ala Leu Pro Leu Thr Thr Val Glu Arg Asn Glu Lys
        195                 200                 205

Phe Tyr Asp Cys Cys Pro Glu Pro Tyr Pro Asp Val His Phe Tyr Leu
    210                 215                 220

His Met Arg Arg Thr Leu Tyr Tyr Gly Phe Asn Leu Ile Met Pro
225                 230                 235                 240

Cys Ile Leu Thr Thr Leu Met Thr Leu Leu Gly Phe Thr Leu Pro Pro
                245                 250                 255

Asp Ala Gly Glu Lys Ile Thr Leu Gln Ile Thr Val Leu Leu Ser Ile
            260                 265                 270

Cys Phe Phe Leu Ser Ile Val Ser Glu Met Ser Pro Pro Thr Ser Glu
        275                 280                 285

Ala Val Pro Leu Leu Gly Ile Phe Phe Thr Cys Cys Met Ile Val Val
    290                 295                 300

Thr Ala Ser Thr Val Phe Thr Val Tyr Val Leu Asn Leu His Tyr Arg
305                 310                 315                 320

Thr Pro Glu Thr His Glu Met Gly Pro Trp Thr Arg Asn Leu Leu Leu
                325                 330                 335

Tyr Trp Ile Pro Trp Ile Leu Arg Met Lys Arg Pro Gly His Asn Leu
            340                 345                 350

Thr Tyr Ala Ser Leu Pro Ser Leu Phe Thr Ser Lys Pro Asn Arg His
        355                 360                 365

Ser Glu Ser Leu Ile Arg Asn Ile Lys Asp Asn Glu His Ser Leu Ser
    370                 375                 380

Arg Ala Asn Ser Phe Asp Ala Asp Cys Arg Leu Asn Gln Tyr Ile Met
385                 390                 395                 400

Thr Gln Ser Val Ser Asn Gly Leu Thr Ser Ile Gly Ser Ile Pro Ser
                405                 410                 415

Thr Met Ile Ser Ser Ala Asn Gly Thr Thr Asp Val Ser Gln Gln
            420                 425                 430

Ala Thr Leu Leu Ile Leu His Arg Ile Tyr His Glu Leu Lys Ile Val
        435                 440                 445

Thr Lys Arg Met Ile Glu Gly Asp Lys Glu Gln Ala Ser Asn Asn
    450                 455                 460

Trp Lys Phe Ala Ala Met Val Val Asp Arg Leu Cys Leu Tyr Val Phe
465                 470                 475                 480

Thr Ile Phe Ile Ile Ala Ser Thr Ile Gly Ile Phe Trp Ser Ala Pro
                485                 490                 495

Tyr Leu Val Ala
            500

<210> SEQ ID NO 21
<211> LENGTH: 514

```
<212> TYPE: PRT
<213> ORGANISM: Artificial Sequence
<220> FEATURE:
<223> OTHER INFORMATION: EGT55171 hypothetical protein CAEBREN_30258
      [Caenorhabditis brenneri]

<400> SEQUENCE: 21
```

| | | | | | | | | | | | | | | | |
|---|---|---|---|---|---|---|---|---|---|---|---|---|---|---|---|
| Met | Ser | Val | Cys | Ala | Leu | Leu | Leu | Thr | Cys | Ala | Leu | Phe | Ala | Ala | Pro |
| 1 | | | | 5 | | | | | 10 | | | | | 15 | |
| Ala | Phe | Gly | Ser | Leu | Gln | Glu | Arg | Arg | Leu | Tyr | Glu | Asp | Leu | Met | Arg |
| | | | 20 | | | | | 25 | | | | | 30 | | |
| Asn | Tyr | Asn | Asn | Leu | Glu | Arg | Pro | Val | Ala | Asn | His | Ser | Glu | Pro | Val |
| | | 35 | | | | | 40 | | | | | 45 | | | |
| Thr | Val | His | Leu | Lys | Val | Ala | Leu | Gln | Gln | Ile | Ile | Asp | Val | Asp | Glu |
| | 50 | | | | | 55 | | | | | 60 | | | | |
| Lys | Asn | Gln | Val | Val | Tyr | Val | Asn | Ala | Trp | Leu | Asp | Tyr | Val | Arg | Phe |
| 65 | | | | | 70 | | | | | 75 | | | | | 80 |
| Ser | Thr | Pro | Gln | Ser | Ser | Val | Thr | Leu | Phe | Phe | Gln | Thr | Trp | Lys | Asp |
| | | | | 85 | | | | | 90 | | | | | 95 | |
| Tyr | Asn | Leu | Val | Trp | Asp | Gln | Ala | Glu | Tyr | Gly | Asn | Ile | Thr | Asp | Val |
| | | | 100 | | | | | 105 | | | | | 110 | | |
| Arg | Phe | Pro | Ala | Gly | Lys | Ile | Trp | Lys | Pro | Asp | Val | Leu | Leu | Tyr | Asn |
| | | 115 | | | | | 120 | | | | | 125 | | | |
| Ser | Val | Asp | Thr | Asn | Phe | Asp | Ser | Thr | Tyr | Gln | Thr | Asn | Met | Ile | Val |
| | 130 | | | | | 135 | | | | | 140 | | | | |
| Tyr | Ser | Ser | Gly | Leu | Val | His | Trp | Val | Pro | Pro | Gly | Ile | Phe | Lys | Ile |
| 145 | | | | | 150 | | | | | 155 | | | | | 160 |
| Ser | Cys | Lys | Ile | Asp | Ile | Gln | Trp | Phe | Pro | Phe | Asp | Glu | Gln | Lys | Cys |
| | | | | 165 | | | | | 170 | | | | | 175 | |
| Phe | Phe | Lys | Phe | Gly | Ser | Trp | Thr | Tyr | Asp | Gly | Tyr | Lys | Leu | Asp | Leu |
| | | | 180 | | | | | 185 | | | | | 190 | | |
| Gln | Pro | Ala | Thr | Gly | Gly | Phe | Asp | Ile | Ser | Glu | Tyr | Leu | Pro | Asn | Gly |
| | | 195 | | | | | 200 | | | | | 205 | | | |
| Glu | Trp | Ala | Leu | Pro | Leu | Thr | Thr | Val | Glu | Arg | Asn | Glu | Lys | Phe | Tyr |
| | 210 | | | | | 215 | | | | | 220 | | | | |
| Asp | Cys | Cys | Pro | Glu | Pro | Tyr | Pro | Asp | Val | His | Phe | Tyr | Leu | His | Met |
| 225 | | | | | 230 | | | | | 235 | | | | | 240 |
| Arg | Arg | Arg | Thr | Leu | Tyr | Tyr | Gly | Phe | Asn | Leu | Ile | Met | Pro | Cys | Ile |
| | | | | 245 | | | | | 250 | | | | | 255 | |
| Leu | Thr | Thr | Leu | Met | Thr | Leu | Leu | Gly | Phe | Thr | Leu | Pro | Pro | Asp | Ala |
| | | | 260 | | | | | 265 | | | | | 270 | | |
| Gly | Glu | Lys | Ile | Thr | Leu | Gln | Ile | Thr | Val | Leu | Leu | Ser | Ile | Cys | Phe |
| | | 275 | | | | | 280 | | | | | 285 | | | |
| Phe | Leu | Ser | Ile | Val | Ser | Glu | Met | Ser | Pro | Pro | Thr | Ser | Glu | Ala | Val |
| | 290 | | | | | 295 | | | | | 300 | | | | |
| Pro | Leu | Leu | Gly | Ile | Phe | Phe | Thr | Cys | Cys | Met | Ile | Val | Val | Thr | Ala |
| 305 | | | | | 310 | | | | | 315 | | | | | 320 |
| Ser | Thr | Val | Phe | Thr | Val | Tyr | Val | Leu | Asn | Leu | His | Tyr | Arg | Thr | Pro |
| | | | | 325 | | | | | 330 | | | | | 335 | |
| Glu | Thr | His | Asp | Met | Gly | Pro | Trp | Pro | Thr | Arg | Asn | Leu | Leu | Tyr | Trp |
| | | | 340 | | | | | 345 | | | | | 350 | | |
| Ile | Pro | Trp | Ile | Leu | Arg | Met | Lys | Arg | Pro | Gly | His | Asn | Leu | Thr | Tyr |
| | | 355 | | | | | 360 | | | | | 365 | | | |
| Ala | Ser | Leu | Pro | Pro | Leu | Phe | Thr | Ser | Lys | Pro | Asn | Arg | His | Ser | Glu |
| | 370 | | | | | 375 | | | | | 380 | | | | |

```
Ser Leu Ile Arg Asn Ile Lys Asp Asn Glu His Ser Leu Ser Arg Ala
385                 390                 395                 400

Asn Ser Phe Asp Ala Asp Cys Arg Leu Asn Gln Tyr Ile Met Thr Gln
            405                 410                 415

Ser Val Ser Asn Gly Leu Thr Ser Met Ala Ser Ile Pro Ser Thr Met
        420                 425                 430

Ile Ser Ser Ala Asn Gly Thr Ser Thr Asp Val Ser Gln Gln Ala Thr
        435                 440                 445

Leu Leu Ile Leu His Arg Ile Tyr His Glu Leu Lys Ile Val Thr Lys
450                 455                 460

Arg Met Ile Glu Gly Asp Lys Glu Gln Ala Ser Asn Asn Trp Lys
465                 470                 475                 480

Phe Ala Ala Met Val Val Asp Arg Leu Cys Leu Tyr Val Phe Thr Ile
                485                 490                 495

Phe Ile Ile Ala Ser Thr Ile Gly Ile Phe Trp Ser Ala Pro Tyr Leu
            500                 505                 510

Val Ala

<210> SEQ ID NO 22
<211> LENGTH: 515
<212> TYPE: PRT
<213> ORGANISM: Artificial Sequence
<220> FEATURE:
<223> OTHER INFORMATION: EGT34516 hypothetical protein CAEBREN_16973
      [Caenorhabditis brenneri]

<400> SEQUENCE: 22

Met Ser Val Cys Ala Leu Leu Thr Cys Ala Leu Phe Ala Ala Pro
1               5                   10                  15

Ala Leu Gly Ser Leu Gln Glu Arg Leu Tyr Glu Asp Leu Met Arg
                20                  25                  30

Asn Tyr Asn Asn Leu Glu Arg Pro Val Ala Asn His Ser Glu Pro Val
            35                  40                  45

Thr Val His Leu Lys Val Ala Leu Gln Gln Ile Ile Asp Val Asp Glu
50                  55                  60

Lys Asn Gln Val Val Tyr Val Asn Ala Trp Leu Asp Tyr Thr Trp Lys
65                  70                  75                  80

Asp Tyr Asn Leu Val Trp Asp Gln Ala Glu Tyr Gly Asn Ile Thr Asp
                85                  90                  95

Val Arg Phe Pro Ala Gly Lys Ile Trp Lys Pro Asp Val Leu Leu Tyr
            100                 105                 110

Asn Ser Val Asp Thr Asn Phe Asp Ser Thr Tyr Gln Thr Asn Met Ile
        115                 120                 125

Val Tyr Ser Ser Gly Leu Val His Trp Val Pro Pro Gly Ile Phe Lys
130                 135                 140

Ile Ser Cys Lys Ile Asp Ile Gln Trp Phe Pro Phe Asp Glu Gln Lys
145                 150                 155                 160

Cys Phe Phe Lys Phe Gly Ser Trp Thr Tyr Asp Gly Tyr Lys Leu Asp
                165                 170                 175

Leu Gln Pro Ala Thr Gly Gly Phe Asp Ile Ser Glu Tyr Leu Pro Asn
            180                 185                 190

Gly Glu Trp Ala Leu Pro Leu Thr Thr Val Glu Arg Asn Glu Lys Phe
        195                 200                 205

Tyr Asp Cys Cys Pro Glu Pro Tyr Pro Asp Val His Phe Tyr Leu His
210                 215                 220
```

Met Arg Arg Arg Thr Leu Tyr Tyr Gly Phe Asn Leu Ile Met Pro Cys
225                 230                 235                 240

Ile Leu Thr Thr Leu Met Thr Leu Leu Gly Phe Thr Leu Pro Pro Asp
            245                 250                 255

Ala Gly Glu Lys Ile Thr Leu Gln Ile Thr Val Leu Leu Ser Ile Cys
        260                 265                 270

Phe Phe Leu Ser Ile Val Ser Glu Met Ser Pro Pro Thr Ser Glu Ala
    275                 280                 285

Val Pro Leu Leu Gly Ile Phe Phe Thr Cys Cys Met Ile Val Val Thr
290                 295                 300

Ala Ser Thr Val Phe Thr Val Tyr Val Leu Asn Leu His Tyr Arg Thr
305                 310                 315                 320

Pro Glu Thr His Asp Met Gly Pro Trp Val Thr Ile Leu Phe Phe Lys
            325                 330                 335

Thr Pro Asp Ile Gln Lys Met Leu Gln Thr Arg Asn Leu Leu Leu Tyr
        340                 345                 350

Trp Ile Pro Trp Ile Leu Arg Met Lys Arg Pro Gly His Asn Leu Thr
    355                 360                 365

Tyr Ala Ser Leu Pro Pro Leu Phe Thr Ser Lys Pro Asn Arg His Ser
370                 375                 380

Glu Ser Leu Ile Arg Asn Ile Lys Asp Asn Glu His Ser Leu Ser Arg
385                 390                 395                 400

Ala Asn Ser Phe Asp Ala Asp Cys Arg Leu Asn Gln Tyr Ile Met Thr
            405                 410                 415

Gln Ser Val Ser Asn Gly Leu Thr Ser Met Ala Ser Ile Pro Ser Thr
        420                 425                 430

Met Ile Ser Ser Ala Asn Gly Thr Ser Thr Asp Val Ser Gln Gln Ala
    435                 440                 445

Thr Leu Leu Ile Leu His Arg Ile Tyr His Glu Leu Lys Ile Val Thr
450                 455                 460

Lys Arg Met Ile Glu Gly Asp Lys Glu Glu Gln Ala Ser Asn Asn Trp
465                 470                 475                 480

Lys Phe Ala Ala Met Val Val Asp Arg Leu Cys Leu Tyr Val Phe Thr
            485                 490                 495

Ile Phe Ile Ile Ala Ser Thr Ile Gly Ile Phe Trp Ser Ala Pro Tyr
        500                 505                 510

Leu Val Ala
        515

<210> SEQ ID NO 23
<211> LENGTH: 497
<212> TYPE: PRT
<213> ORGANISM: Artificial Sequence
<220> FEATURE:
<223> OTHER INFORMATION: XP_002635324 C. briggsae CBR-ACR-16 protein,
      partial

<400> SEQUENCE: 23

Ser Val Cys Ala Leu Leu Leu Ser Cys Ala Leu Phe Leu Val Ala His
1               5                   10                  15

Gly Ser Leu Gln Glu Arg Arg Leu Tyr Glu Asp Leu Met Arg Asn Tyr
            20                  25                  30

Asn Asn Leu Glu Arg Pro Val Ala Asn His Ser Glu Pro Val Thr Val
        35                  40                  45

His Leu Lys Val Ala Leu Gln Gln Ile Ile Asp Val Asp Glu Lys Asn

```
            50                  55                  60
Gln Val Tyr Val Asn Ala Trp Leu Asp Tyr Thr Trp Lys Asp Tyr
 65                  70                  75                  80

Asn Leu Val Trp Asp Gln Ala Glu Tyr Gly Asn Ile Thr Asp Val Arg
                 85                  90                  95

Phe Pro Ala Gly Lys Ile Trp Lys Pro Asp Val Leu Leu Tyr Asn Ser
            100                 105                 110

Val Asp Thr Asn Phe Asp Ser Thr Tyr Gln Thr Asn Met Ile Val Tyr
        115                 120                 125

Ser Ser Gly Leu Val His Trp Val Pro Pro Gly Ile Phe Lys Ile Ser
    130                 135                 140

Cys Lys Ile Asp Ile Gln Trp Phe Pro Phe Asp Glu Gln Lys Cys Phe
145                 150                 155                 160

Phe Lys Phe Gly Ser Trp Thr Tyr Asp Gly Tyr Lys Leu Asp Leu Gln
                165                 170                 175

Pro Ala Thr Gly Gly Phe Asp Ile Ser Glu Tyr Leu Pro Asn Gly Glu
            180                 185                 190

Trp Ala Leu Pro Leu Thr Thr Val Glu Arg Asn Glu Lys Phe Tyr Asp
        195                 200                 205

Cys Cys Pro Glu Pro Tyr Pro Asp Val His Phe Tyr Leu His Met Arg
    210                 215                 220

Arg Arg Thr Leu Tyr Tyr Gly Phe Asn Leu Ile Met Pro Cys Ile Leu
225                 230                 235                 240

Thr Thr Leu Met Thr Leu Leu Gly Phe Thr Leu Pro Pro Asp Ala Gly
                245                 250                 255

Glu Lys Ile Thr Leu Gln Ile Thr Val Leu Leu Ser Ile Cys Phe Phe
            260                 265                 270

Leu Ser Ile Val Ser Glu Met Ser Pro Pro Thr Ser Glu Ala Val Pro
        275                 280                 285

Leu Leu Gly Ile Phe Phe Thr Cys Cys Met Ile Val Val Thr Ala Ser
    290                 295                 300

Thr Val Phe Thr Val Tyr Val Leu Asn Leu His Tyr Arg Thr Pro Glu
305                 310                 315                 320

Thr His Asp Met Gly Pro Trp Thr Arg Asn Leu Leu Leu Tyr Trp Ile
                325                 330                 335

Pro Trp Ile Leu Arg Met Lys Arg Pro Gly His Asn Leu Thr Tyr Ala
            340                 345                 350

Ser Leu Pro Ser Leu Phe Ala Ser Lys Pro Asn Arg His Ser Glu Ser
        355                 360                 365

Leu Ile Arg Asn Ile Lys Asp Asn Glu His Ser Leu Ser Arg Ala Asn
    370                 375                 380

Ser Phe Asp Ala Asp Cys Arg Leu Asn Gln Tyr Ile Met Thr Gln Ser
385                 390                 395                 400

Val Ser Asn Gly Leu Thr Ser Met Gly Ser Ile Pro Ser Thr Met Ile
                405                 410                 415

Ser Ser Thr Asn Gly Ala Leu Thr Asp Val Ser Gln Gln Ala Thr Leu
            420                 425                 430

Leu Ile Leu His Arg Ile Tyr His Glu Leu Lys Ile Val Thr Lys Arg
        435                 440                 445

Met Ile Glu Gly Asp Lys Glu Glu Gln Ala Ser Asn Asn Trp Lys Phe
    450                 455                 460

Ala Ala Met Val Val Asp Arg Leu Cys Leu Tyr Val Phe Thr Ile Phe
465                 470                 475                 480
```

```
Ile Ile Ala Ser Thr Ile Gly Ile Phe Trp Ser Ala Pro Tyr Leu Val
                485                 490                 495

Ala

<210> SEQ ID NO 24
<211> LENGTH: 499
<212> TYPE: PRT
<213> ORGANISM: Artificial Sequence
<220> FEATURE:
<223> OTHER INFORMATION: A8WQK3 Acetylcholine receptor subunit
      alpha-type acr-16

<400> SEQUENCE: 24

Met Ser Ser Val Cys Ala Leu Leu Ser Cys Ala Leu Phe Leu Val
1               5                   10                  15

Ala His Gly Ser Leu Gln Glu Arg Arg Leu Tyr Glu Asp Leu Met Arg
                20                  25                  30

Asn Tyr Asn Asn Leu Glu Arg Pro Val Ala Asn His Ser Glu Pro Val
                35                  40                  45

Thr Val His Leu Lys Val Ala Leu Gln Gln Ile Ile Asp Val Asp Glu
        50                  55                  60

Lys Asn Gln Val Val Tyr Val Asn Ala Trp Leu Asp Tyr Thr Trp Lys
65                  70                  75                  80

Asp Tyr Asn Leu Val Trp Asp Gln Ala Glu Tyr Gly Asn Ile Thr Asp
                85                  90                  95

Val Arg Phe Pro Ala Gly Lys Ile Trp Lys Pro Asp Val Leu Leu Tyr
                100                 105                 110

Asn Ser Val Asp Thr Asn Phe Asp Ser Thr Tyr Gln Thr Asn Met Ile
                115                 120                 125

Val Tyr Ser Ser Gly Leu Val His Trp Val Pro Pro Gly Ile Phe Lys
        130                 135                 140

Ile Ser Cys Lys Ile Asp Ile Gln Trp Phe Pro Phe Asp Glu Gln Lys
145                 150                 155                 160

Cys Phe Phe Lys Phe Gly Ser Trp Thr Tyr Asp Gly Tyr Lys Leu Asp
                165                 170                 175

Leu Gln Pro Ala Thr Gly Gly Phe Asp Ile Ser Glu Tyr Leu Pro Asn
                180                 185                 190

Gly Glu Trp Ala Leu Pro Leu Thr Thr Val Glu Arg Asn Glu Lys Phe
                195                 200                 205

Tyr Asp Cys Cys Pro Glu Pro Tyr Pro Asp Val His Phe Tyr Leu His
        210                 215                 220

Met Arg Arg Arg Thr Leu Tyr Tyr Gly Phe Asn Leu Ile Met Pro Cys
225                 230                 235                 240

Ile Leu Thr Thr Leu Met Thr Leu Leu Gly Phe Thr Leu Pro Pro Asp
                245                 250                 255

Ala Gly Glu Lys Ile Thr Leu Gln Ile Thr Val Leu Leu Ser Ile Cys
                260                 265                 270

Phe Phe Leu Ser Ile Val Ser Glu Met Ser Pro Thr Ser Glu Ala
                275                 280                 285

Val Pro Leu Leu Gly Ile Phe Phe Thr Cys Met Ile Val Val Thr
                290                 295                 300

Ala Ser Thr Val Phe Thr Val Tyr Val Leu Asn Leu His Tyr Arg Thr
305                 310                 315                 320

Pro Glu Thr His Asp Met Gly Pro Trp Thr Arg Asn Leu Leu Leu Tyr
                325                 330                 335
```

Trp Ile Pro Trp Ile Leu Arg Met Lys Arg Pro Gly His Asn Leu Thr
            340                 345                 350

Tyr Ala Ser Leu Pro Ser Leu Phe Ala Ser Lys Pro Asn Arg His Ser
            355                 360                 365

Glu Ser Leu Ile Arg Asn Ile Lys Asp Asn Glu His Ser Leu Ser Arg
370                 375                 380

Ala Asn Ser Phe Asp Ala Asp Cys Arg Leu Asn Gln Tyr Ile Met Thr
385                 390                 395                 400

Gln Ser Val Ser Asn Gly Leu Thr Ser Met Gly Ser Ile Pro Ser Thr
                405                 410                 415

Met Ile Ser Ser Thr Asn Gly Ala Leu Thr Asp Val Ser Gln Gln Ala
            420                 425                 430

Thr Leu Leu Ile Leu His Arg Ile Tyr His Glu Leu Lys Ile Val Thr
            435                 440                 445

Lys Arg Met Ile Glu Gly Asp Lys Glu Glu Gln Ala Ser Asn Asn Trp
450                 455                 460

Lys Phe Ala Ala Met Val Val Asp Arg Leu Cys Leu Tyr Val Phe Thr
465                 470                 475                 480

Ile Phe Ile Ile Ala Ser Thr Ile Gly Ile Phe Trp Ser Ala Pro Tyr
                485                 490                 495

Leu Val Ala

<210> SEQ ID NO 25
<211> LENGTH: 506
<212> TYPE: PRT
<213> ORGANISM: Artificial Sequence
<220> FEATURE:
<223> OTHER INFORMATION: EJD73698 nicotinic acetylcholine receptor alpha
      34E [Loa loa]

<400> SEQUENCE: 25

Met Leu Gln Ser Trp Thr Asn His Ser Leu Val Trp Cys Leu His Leu
1               5                   10                  15

Ile Leu Leu Phe Ala Phe Leu Gln Met Ile Thr Gly Ser Tyr His Glu
            20                  25                  30

Arg Arg Leu Tyr Asp Asp Leu Met Lys Asn Tyr Asn Leu Glu Arg
            35                  40                  45

Pro Val Gln Asn His Ser Gln Pro Val Val Tyr Leu Lys Val Ser
        50                  55                  60

Leu Gln Gln Ile Ile Asp Val Asp Glu Lys Asn Gln Ile Val Tyr Val
65                  70                  75                  80

Asn Ala Trp Leu Asp Phe Ala Trp Asn Asp Tyr Lys Leu Arg Trp Asp
                85                  90                  95

Lys Thr Lys Tyr Gly Asn Ile Thr Asp Val Arg Phe Pro Ala Gly Lys
            100                 105                 110

Ile Trp Lys Pro Asp Val Leu Leu Tyr Asn Ser Val Asp Ala Asn Phe
        115                 120                 125

Asp Ser Thr Tyr Pro Thr Asn Met Ile Val Tyr Asn Thr Gly Asp Ile
    130                 135                 140

Ser Trp Ile Pro Pro Ala Ile Phe Lys Ile Ser Cys Lys Ile Asn Ile
145                 150                 155                 160

Glu Trp Phe Pro Phe Asp Glu Gln Arg Cys Phe Phe Lys Phe Gly Ser
                165                 170                 175

Trp Thr Tyr Gly Gly Asp Lys Leu Asp Leu Gln Pro Gly Lys Gly Gly
            180                 185                 190

Phe Asp Ile Ser Glu Tyr Met Pro Ser Gly Glu Trp Ala Leu Pro Met
        195                 200                 205

Thr Thr Val Ser Arg Thr Val Lys Phe Tyr Glu Cys Cys Pro Glu Pro
210                 215                 220

Tyr Pro Asp Leu Lys Phe Tyr Leu His Leu Arg Arg Arg Thr Leu Tyr
225                 230                 235                 240

Tyr Gly Phe Asn Leu Ile Met Pro Cys Ile Leu Thr Thr Met Met Thr
                245                 250                 255

Leu Leu Gly Phe Thr Leu Pro Pro Asp Ala Gly Glu Lys Ile Thr Leu
            260                 265                 270

Gln Ile Thr Val Leu Leu Ser Ile Cys Phe Phe Leu Ser Ile Val Ser
        275                 280                 285

Glu Met Ser Pro Pro Thr Ser Glu Ala Val Pro Leu Leu Gly Ile Phe
290                 295                 300

Phe Ser Cys Cys Met Ile Val Val Thr Ala Ser Thr Val Phe Thr Val
305                 310                 315                 320

Tyr Val Leu Asn Leu His Tyr Arg Thr Ser Glu Thr His Glu Met Gly
                325                 330                 335

Thr Leu Thr Lys Thr Leu Leu Leu Tyr Trp Leu Pro Tyr Leu Leu Arg
            340                 345                 350

Ile Asn Arg Pro Gly Val Asn Leu Ser Trp Lys Thr Leu Pro Ser Leu
        355                 360                 365

Phe Pro Ser Arg Lys Pro Thr Thr His Ser Glu Ser Leu Ile Arg Asn
370                 375                 380

Ile Lys Glu Ala Glu Ser Asn Ser Arg Ser Asn Ser Leu Asp Ala Asp
385                 390                 395                 400

Cys Arg Val Cys Gln Tyr Met Ser Gly Ile Ser Asn Gly Lys Ser Pro
                405                 410                 415

Ile Ser Thr Val Ile Asn Gly Pro Thr Leu Ser Gln Thr Asn Ser Ser
            420                 425                 430

Thr Asp Ile Gly Gln Gln Ala Thr Leu Leu Val Leu Gln Arg Ile Tyr
        435                 440                 445

Gln Glu Leu Lys Met Ile Thr Lys Arg Met Met Asp Ala Glu Lys Asp
450                 455                 460

Asp Ala Lys Ala Asn Asn Trp Lys Phe Ala Ala Ile Val Val Asp Arg
465                 470                 475                 480

Leu Cys Leu Tyr Ile Phe Thr Ile Phe Ile Ile Ala Ser Ser Cys Gly
                485                 490                 495

Ile Leu Leu Ser Ala Pro Tyr Phe Ile Ala
            500                 505

<210> SEQ ID NO 26
<211> LENGTH: 368
<212> TYPE: PRT
<213> ORGANISM: Artificial Sequence
<220> FEATURE:
<223> OTHER INFORMATION: protein RIC-3 isoform 1 [Gorilla gorilla
      gorilla]

<400> SEQUENCE: 26

Met Ala Tyr Ser Thr Val Gln Arg Val Ala Leu Ala Ser Gly Leu Val
1               5                   10                  15

Leu Ala Leu Ser Leu Leu Leu Pro Lys Ala Phe Leu Ser Arg Gly Lys
            20                  25                  30

Arg Gln Glu Pro Pro Pro Thr Pro Glu Gly Lys Leu Gly Arg Phe Pro

```
            35                  40                  45
Pro Met Met His His His Gln Ala Pro Ser Asp Gly Gln Thr Pro Gly
 50                  55                  60

Ala Arg Phe Gln Arg Ser His Leu Ala Glu Ala Phe Ala Lys Ala Lys
 65                  70                  75                  80

Gly Ser Gly Gly Gly Ala Gly Gly Gly Ser Gly Arg Gly Leu Met
                 85                  90                  95

Gly Gln Ile Ile Pro Ile Tyr Gly Phe Gly Ile Phe Leu Tyr Ile Leu
                100                 105                 110

Tyr Ile Leu Phe Lys Leu Ser Lys Gly Lys Thr Thr Ala Glu Asp Gly
                115                 120                 125

Lys Cys Tyr Thr Ala Thr Pro Gly Asn Thr His Arg Lys Ile Thr Ser
130                 135                 140

Phe Glu Leu Ala Gln Leu Gln Glu Lys Leu Lys Glu Thr Glu Ala Ala
145                 150                 155                 160

Met Glu Lys Leu Ile Asn Arg Val Gly Pro Asn Gly Glu Arg Ala Gln
                165                 170                 175

Thr Val Thr Ser Asp Gln Glu Lys Arg Leu Leu His Gln Leu Arg Glu
                180                 185                 190

Ile Thr Arg Val Met Lys Glu Gly Lys Phe Ile Asp Arg Phe Ser Pro
                195                 200                 205

Glu Lys Glu Ala Glu Ala Pro Tyr Met Glu Asp Trp Gly Tyr
210                 215                 220

Pro Glu Glu Thr Tyr Pro Ile Tyr Asp Leu Ser Asp Cys Ile Lys Arg
225                 230                 235                 240

Arg Gln Glu Thr Ile Leu Val Asp Tyr Pro Asp Pro Lys Glu Leu Ser
                245                 250                 255

Ala Glu Glu Ile Ala Glu Arg Met Gly Met Ile Glu Glu Glu Ser
                260                 265                 270

Asp His Leu Gly Trp Glu Ser Leu Pro Thr Asp Pro Arg Ala Gln Glu
                275                 280                 285

Asp Asn Ser Val Thr Ser Cys Asp Pro Lys Pro Glu Thr Cys Ser Cys
290                 295                 300

Cys Phe His Glu Asp Glu Asp Pro Ala Val Leu Ala Glu Asn Ala Gly
305                 310                 315                 320

Phe Ser Ala Asp Ser Tyr Pro Glu Gln Glu Thr Thr Lys Glu Glu
                325                 330                 335

Trp Ser Gln Asp Phe Lys Asp Gly Leu Gly Ile Ser Thr Asp Lys
                340                 345                 350

Ala Tyr Thr Gly Ser Met Leu Arg Lys Arg Asn Pro Gln Gly Leu Glu
                355                 360                 365

<210> SEQ ID NO 27
<211> LENGTH: 397
<212> TYPE: PRT
<213> ORGANISM: Artificial Sequence
<220> FEATURE:
<223> OTHER INFORMATION: protein RIC-3 isoform X2 [Homo sapiens]

<400> SEQUENCE: 27

Met Ala Tyr Ser Thr Val Gln Arg Val Ala Leu Ala Ser Gly Leu Val
 1                   5                  10                  15

Leu Ala Leu Ser Leu Leu Leu Pro Lys Ala Phe Leu Ser Arg Gly Lys
                 20                  25                  30

Arg Gln Glu Pro Pro Pro Thr Pro Glu Gly Lys Leu Gly Arg Phe Pro
```

```
            35                  40                  45
Pro Met Met His His His Gln Ala Pro Ser Asp Gly Gln Thr Pro Gly
 50                  55                  60

Ala Arg Phe Gln Arg Ser His Leu Ala Glu Ala Phe Ala Lys Ala Lys
 65                  70                  75                  80

Gly Ser Gly Gly Gly Ala Gly Gly Gly Ser Gly Arg Gly Leu Met
                 85                  90                  95

Gly Gln Ile Ile Pro Ile Tyr Gly Phe Gly Ile Phe Leu Tyr Ile Leu
                100                 105                 110

Tyr Ile Leu Phe Lys Leu Ser Lys Gly Lys Thr Thr Ala Glu Asp Gly
                115                 120                 125

Lys Cys Tyr Thr Ala Met Pro Gly Asn Thr His Arg Lys Ile Thr Ser
130                 135                 140

Phe Glu Leu Ala Gln Leu Gln Glu Lys Leu Lys Glu Thr Glu Ala Ala
145                 150                 155                 160

Met Glu Lys Leu Ile Asn Arg Val Gly Pro Asn Gly Glu Ser Thr Gln
                165                 170                 175

Thr Asp His Ser Asp Val Tyr Val His Cys Leu Gly Val Phe Thr Thr
                180                 185                 190

Lys Trp Leu Asp Cys Leu Ile Phe Leu Ser Arg Ala Gln Thr Val Thr
                195                 200                 205

Ser Asp Gln Glu Lys Arg Leu Leu His Gln Leu Arg Glu Ile Thr Arg
210                 215                 220

Val Met Lys Glu Gly Lys Phe Ile Asp Arg Phe Ser Pro Glu Lys Glu
225                 230                 235                 240

Ala Glu Glu Ala Pro Tyr Met Glu Asp Trp Glu Gly Tyr Pro Glu Glu
                245                 250                 255

Thr Tyr Pro Ile Tyr Asp Leu Ser Asp Cys Ile Lys Arg Arg Gln Glu
                260                 265                 270

Thr Ile Leu Val Asp Tyr Pro Asp Pro Lys Glu Leu Ser Ala Glu Glu
                275                 280                 285

Ile Ala Glu Arg Met Gly Met Ile Glu Glu Glu Glu Ser Asp His Leu
290                 295                 300

Gly Trp Glu Ser Leu Pro Thr Asp Pro Arg Ala Gln Glu Asp Asn Ser
305                 310                 315                 320

Val Thr Ser Cys Asp Pro Lys Pro Glu Thr Cys Ser Cys Phe His
                325                 330                 335

Glu Asp Glu Asp Pro Ala Val Leu Ala Glu Asn Ala Gly Phe Ser Ala
                340                 345                 350

Asp Ser Tyr Pro Glu Gln Glu Glu Thr Thr Lys Glu Glu Trp Ser Gln
                355                 360                 365

Asp Phe Lys Asp Glu Gly Leu Gly Ile Ser Thr Asp Lys Ala Tyr Thr
                370                 375                 380

Gly Ser Met Leu Arg Lys Arg Asn Pro Gln Gly Leu Glu
385                 390                 395

<210> SEQ ID NO 28
<211> LENGTH: 368
<212> TYPE: PRT
<213> ORGANISM: Artificial Sequence
<220> FEATURE:
<223> OTHER INFORMATION: protein RIC-3 isoform X3 [Nomascus leucogenys]

<400> SEQUENCE: 28

Met Ala Tyr Ser Thr Val Gln Arg Val Ala Leu Val Ser Gly Leu Val
```

```
1               5                   10                  15
Leu Ala Leu Ser Leu Leu Leu Pro Lys Ala Phe Leu Ser Arg Gly Lys
                20                  25                  30
Arg Gln Glu Pro Pro Thr Pro Glu Gly Lys Leu Gly Arg Phe Pro
            35                  40                  45
Pro Met Ile His His His Gln Val Pro Ser Asp Gly Gln Thr Pro Gly
            50                  55                  60
Pro Arg Phe Gln Arg Ser His Leu Ala Glu Ala Phe Ala Lys Ala Lys
 65                  70                  75                  80
Gly Ser Gly Gly Gly Ala Gly Gly Gly Ser Gly Arg Gly Leu Met
                85                  90                  95
Gly Gln Ile Ile Pro Ile Tyr Gly Phe Gly Ile Phe Leu Tyr Ile Leu
                100                 105                 110
Tyr Ile Leu Phe Lys Leu Ser Lys Gly Lys Thr Thr Ala Glu Val Gly
                115                 120                 125
Lys Cys Tyr Thr Ala Thr Pro Gly Asn Thr His Arg Lys Ile Thr Ser
        130                 135                 140
Phe Glu Leu Ala Gln Leu Gln Glu Lys Leu Lys Glu Thr Glu Ala Ala
145                 150                 155                 160
Met Glu Lys Leu Ile Asn Arg Val Gly Pro Asn Gly Glu Arg Thr Gln
                165                 170                 175
Thr Val Thr Ser Asp Gln Glu Lys Arg Leu Leu His Gln Leu Arg Glu
            180                 185                 190
Ile Thr Arg Val Met Lys Glu Gly Lys Phe Ile Asp Arg Phe Ser Pro
        195                 200                 205
Glu Lys Glu Ala Glu Glu Ala Pro Tyr Met Glu Asp Trp Glu Gly Tyr
210                 215                 220
Pro Glu Glu Thr Tyr Pro Ile Tyr Asp Leu Ser Asp Cys Ile Lys His
225                 230                 235                 240
Arg Gln Glu Thr Ile Leu Val Asp Tyr Pro Asp Pro Lys Glu Leu Ser
                245                 250                 255
Ala Glu Glu Ile Ala Glu Arg Met Gly Met Ile Glu Glu Glu Ser
            260                 265                 270
Asp His Leu Gly Trp Glu Ser Leu Pro Thr Asp Pro Arg Ala Gln Glu
        275                 280                 285
Asp Asn Ser Val Thr Ser Cys Asp Pro Lys Pro Glu Thr Cys Ser Cys
        290                 295                 300
Cys Phe His Glu Asp Glu Asp Pro Ala Val Leu Ala Glu Asn Ala Gly
305                 310                 315                 320
Phe Ser Ala Asp Ser Tyr Pro Glu Gln Glu Glu Thr Thr Lys Glu Glu
                325                 330                 335
Trp Ser Gln Asp Phe Lys Asp Glu Glu Leu Gly Ile Ser Thr Asp Lys
                340                 345                 350
Ala Tyr Thr Gly Ser Met Leu Arg Lys Arg Asn Pro Gln Gly Leu Glu
            355                 360                 365
```

<210> SEQ ID NO 29
<211> LENGTH: 397
<212> TYPE: PRT
<213> ORGANISM: Artificial Sequence
<220> FEATURE:
<223> OTHER INFORMATION: protein RIC-3 isoform X1 [Nomascus leucogenys]

<400> SEQUENCE: 29

Met Ala Tyr Ser Thr Val Gln Arg Val Ala Leu Val Ser Gly Leu Val

```
                1               5                    10                   15
            Leu Ala Leu Ser Leu Leu Leu Pro Lys Ala Phe Leu Ser Arg Gly Lys
                            20                  25                  30
            Arg Gln Glu Pro Pro Thr Pro Glu Gly Lys Leu Gly Arg Phe Pro
                        35                  40                  45
            Pro Met Ile His His His Gln Val Pro Ser Asp Gly Gln Thr Pro Gly
                        50                  55                  60
            Pro Arg Phe Gln Arg Ser His Leu Ala Glu Ala Phe Ala Lys Ala Lys
            65                  70                  75                  80
            Gly Ser Gly Gly Gly Ala Gly Gly Gly Ser Gly Arg Gly Leu Met
                                85                  90                  95
            Gly Gln Ile Ile Pro Ile Tyr Gly Phe Gly Ile Phe Leu Tyr Ile Leu
                            100                 105                 110
            Tyr Ile Leu Phe Lys Leu Ser Lys Gly Lys Thr Thr Ala Glu Val Gly
                            115                 120                 125
            Lys Cys Tyr Thr Ala Thr Pro Gly Asn Thr His Arg Lys Ile Thr Ser
                    130                 135                 140
            Phe Glu Leu Ala Gln Leu Gln Glu Lys Leu Lys Glu Thr Glu Ala Ala
            145                 150                 155                 160
            Met Glu Lys Leu Ile Asn Arg Val Gly Pro Asn Gly Glu Ser Ile Gln
                            165                 170                 175
            Thr Asp His Ser Asp Val Tyr Val His Cys Leu Gly Val Phe Thr Thr
                        180                 185                 190
            Lys Trp Leu Asp Cys Leu Ile Phe Leu Ser Arg Thr Gln Thr Val Thr
                        195                 200                 205
            Ser Asp Gln Glu Lys Arg Leu Leu His Gln Leu Arg Glu Ile Thr Arg
                    210                 215                 220
            Val Met Lys Glu Gly Lys Phe Ile Asp Arg Phe Ser Pro Glu Lys Glu
            225                 230                 235                 240
            Ala Glu Glu Ala Pro Tyr Met Glu Asp Trp Glu Gly Tyr Pro Glu Glu
                            245                 250                 255
            Thr Tyr Pro Ile Tyr Asp Leu Ser Asp Cys Ile Lys His Arg Gln Glu
                        260                 265                 270
            Thr Ile Leu Val Asp Tyr Pro Asp Pro Lys Glu Leu Ser Ala Glu Glu
                        275                 280                 285
            Ile Ala Glu Arg Met Gly Met Ile Glu Glu Glu Ser Asp His Leu
                    290                 295                 300
            Gly Trp Glu Ser Leu Pro Thr Asp Pro Arg Ala Gln Glu Asp Asn Ser
            305                 310                 315                 320
            Val Thr Ser Cys Asp Pro Lys Pro Glu Thr Cys Ser Cys Cys Phe His
                            325                 330                 335
            Glu Asp Glu Asp Pro Ala Val Leu Ala Glu Asn Ala Gly Phe Ser Ala
                        340                 345                 350
            Asp Ser Tyr Pro Glu Gln Glu Glu Thr Thr Lys Glu Gly Trp Ser Gln
                        355                 360                 365
            Asp Phe Lys Asp Glu Glu Leu Gly Ile Ser Thr Asp Lys Ala Tyr Thr
                    370                 375                 380
            Gly Ser Met Leu Arg Lys Arg Asn Pro Gln Gly Leu Glu
            385                 390                 395

<210> SEQ ID NO 30
<211> LENGTH: 367
<212> TYPE: PRT
<213> ORGANISM: Artificial Sequence
```

<220> FEATURE:
<223> OTHER INFORMATION: protein RIC-3 isoform X2 [Microcebus murinus]

<400> SEQUENCE: 30

```
Met Ala Tyr Ser Thr Val Gln Arg Val Ala Leu Ala Ser Gly Leu Val
1               5                   10                  15

Leu Ala Val Ser Leu Leu Leu Pro Lys Ala Phe Leu Ser Arg Gly Lys
            20                  25                  30

Arg Gln Glu Pro Pro Pro Ala Pro Glu Gly Lys Leu Gly Arg Phe Pro
        35                  40                  45

Pro Met Met His His His Gln Ala Pro Ser Asp Gly Gln Ile Pro Gly
    50                  55                  60

Ala Arg Phe Gln Arg Ser His Leu Ala Glu Ala Phe Ala Lys Ala Lys
65                  70                  75                  80

Gly Ser Gly Gly Gly Thr Gly Gly Gly Ser Gly Arg Ser Leu Met
                85                  90                  95

Gly Gln Ile Ile Pro Ile Tyr Gly Phe Gly Ile Phe Leu Tyr Ile Leu
                100                 105                 110

Tyr Ile Leu Phe Lys Leu Ser Lys Gly Lys Thr Thr Ala Glu Asp Arg
            115                 120                 125

Lys Cys Ser Thr Ala Thr Pro Gly Asn Ala His Arg Lys Ile Thr Asn
        130                 135                 140

Phe Glu Leu Ala Gln Leu Gln Glu Lys Leu Lys Glu Thr Glu Ala
145                 150                 155                 160

Met Glu Lys Leu Ile Asn Arg Val Gly Pro Asn Gly Glu Arg Ala Gln
                165                 170                 175

Thr Val Thr Ser Asp Gln Glu Lys Arg Leu Leu His Gln Leu Arg Glu
            180                 185                 190

Ile Thr Arg Val Met Lys Glu Gly Lys Phe Ile Asp Arg Thr Ser Pro
        195                 200                 205

Glu Lys Glu Ala Glu Ala Pro Tyr Met Glu Asp Trp Glu Gly Tyr
210                 215                 220

Pro Glu Glu Thr Tyr Pro Ile Tyr Asp Leu Ser Asp Cys Ile Lys His
225                 230                 235                 240

Arg Gln Glu Thr Ile Leu Val Asp Tyr Pro Asp Pro Ser Glu Pro Ser
                245                 250                 255

Ala Glu Glu Ile Ala Glu Arg Met Gly Val Ile Glu Glu Glu Ser
            260                 265                 270

Asp His Leu Gly Trp Gln Ser Leu Pro Thr Asp Thr Arg Ala Gln Glu
        275                 280                 285

Asp Asn Ser Val Thr Leu Cys Asp Pro Lys Pro Glu Thr Gly Ser Cys
290                 295                 300

Cys Phe His Glu Glu Asp Pro Ala Val Leu Ala Glu Asn Ala Gly
305                 310                 315                 320

Phe Asn Ala Asp Ser His Glu Gln Glu Glu Thr Thr Lys Glu Glu Trp
                325                 330                 335

Pro Gln Asp Phe Arg Val Glu Gly Leu Gly Leu Asn Val Asp Gln Val
            340                 345                 350

Tyr Thr Gly Ser Met Leu Arg Lys Arg Asn Pro Gln Gly Leu Glu
        355                 360                 365
```

<210> SEQ ID NO 31
<211> LENGTH: 368
<212> TYPE: PRT
<213> ORGANISM: Artificial Sequence
<220> FEATURE:
<223> OTHER INFORMATION: protein RIC-3 isoform X3

<400> SEQUENCE: 31

```
Met Ala Tyr Ser Thr Val Gln Arg Val Thr Leu Ala Ser Gly Leu Val
1               5                   10                  15

Leu Ala Val Ser Leu Leu Pro Lys Ala Phe Leu Ser Arg Gly Lys
            20                  25                  30

Arg Pro Glu Pro Pro Ala Pro Glu Gly Lys Leu Gly Arg Phe Pro
        35              40                  45

Pro Met Met His His His Gln Ala Pro Ser Asp Gly Gln Thr Pro Gly
    50              55                  60

Ala Arg Phe Gln Arg Ser His Leu Ala Glu Ala Phe Ala Lys Ala Lys
65                  70                  75                  80

Gly Ser Gly Gly Gly Thr Gly Gly Gly Ser Gly Arg Gly Leu Met
                85                  90                  95

Gly Gln Ile Ile Pro Ile Tyr Gly Phe Gly Ile Phe Leu Tyr Ile Leu
                100                 105                 110

Tyr Ile Leu Phe Lys Leu Ser Lys Gly Lys Ser Thr Ala Glu Asp Arg
            115                 120                 125

Lys Cys Ser Pro Ala Thr Pro Gly Asn Thr His Arg Lys Ile Thr Asn
    130                 135                 140

Phe Glu Leu Val Gln Leu Gln Glu Lys Leu Lys Glu Thr Glu Ala
145                 150                 155                 160

Met Glu Lys Leu Ile Asn Arg Val Gly Pro Asn Gly Glu Ser Arg Ala
                165                 170                 175

Gln Thr Val Thr Ser Asp Gln Glu Lys Arg Leu Leu His Gln Leu Arg
            180                 185                 190

Glu Ile Thr Arg Val Met Lys Gly Lys Leu Ile Asp Arg Pro Thr
            195                 200                 205

Pro Glu Lys Glu Ala Glu Ala Pro Tyr Met Glu Asp Trp Glu Gly
    210                 215                 220

Tyr Pro Glu Glu Thr Tyr Pro Ile Tyr Asp Leu Ser Asp Cys Ile Lys
225                 230                 235                 240

Arg Arg Gln Glu Thr Ile Leu Val Asp Tyr Pro Asn Pro Gln Glu Pro
                245                 250                 255

Ser Ala Glu Glu Ile Ala Glu Arg Met Gly Val Leu Glu Glu Glu
            260                 265                 270

Ser Asp His Leu Gly Trp Glu Met Pro Thr Asp Pro Arg Ala Gln Glu
    275                 280                 285

Glu Asn Ser Val Thr Phe Cys Asp Pro Lys Pro Glu Thr Cys Ser Cys
    290                 295                 300

Cys Phe Pro Glu Glu Asp Pro Ala Val Leu Ala Glu Asn Ala Gly
305                 310                 315                 320

Phe Ser Ala Asp Ser Tyr Ser Glu Gln Glu Glu Thr Thr Lys Glu Val
                325                 330                 335

Trp Pro Gln Asp Phe Arg Gly Glu Gly Leu Gly Ile Ser Asp Asp Lys
            340                 345                 350

Ala His Pro Gly Gly Met Leu Arg Lys Arg Gly Pro Gln Gly Leu Glu
    355                 360                 365
```

<210> SEQ ID NO 32
<211> LENGTH: 365
<212> TYPE: PRT
<213> ORGANISM: Artificial Sequence
<220> FEATURE:
<223> OTHER INFORMATION: resistance to inhibitors of cholinesterase
      protein 3.2 [Haemonchus contortus]

<400> SEQUENCE: 32

| | | | | | | | | | | | | |
|---|---|---|---|---|---|---|---|---|---|---|---|---|
| Met | Pro | Val | His | Gly | Arg | Glu | Arg | Glu | Arg | Lys | Arg | Arg | Arg | Arg |
| 1 | | | | 5 | | | | | 10 | | | | | 15 |

Met Pro Val His Gly Arg Glu Arg Glu Arg Lys Arg Arg Arg Arg
1               5                   10                  15

Ser Asp Ser Glu Asp Asp Ser Val Phe Thr Gly Trp Lys Leu Gly
            20                  25                  30

Leu Val Val Gly Val Ile Val Ile Cys Phe Ala Met Leu Tyr Pro Thr
            35                  40                  45

Leu Ile His Pro Met Leu Met Ser Leu Leu Gly Arg Ser Pro Pro
        50                  55                  60

Pro Pro Ala Val Pro Ser Arg Pro Pro Ile His Pro Gly Met Gly Gly
65                  70                  75                  80

Pro Gly Gly Gly Arg Pro Gly Gly Pro Ser Arg His Asp Val His Pro
                85                  90                  95

Ala Met Arg Met Ala Gln Gln Ala Glu Thr Gln Ser Ser Gly Arg
                100                 105                 110

Gly Ser Phe Thr Trp Met Leu Pro Leu Tyr Thr Val Gly Val Val Ile
            115                 120                 125

Phe Leu Leu Tyr Thr Leu Phe Lys Ser Lys Gly Lys Arg Lys Arg Arg
        130                 135                 140

Ser Arg Tyr Gly Ser Ser Asp Glu Ser Ser Asp Asp Asp Val Tyr
145                 150                 155                 160

Asn Ser Arg Leu Lys Lys Lys Ile Gly Lys Arg Lys Leu Arg Ser Leu
                165                 170                 175

Gln Glu Arg Leu Gln Gln Thr Glu Glu Ala Met Ser Lys Ile Leu Glu
            180                 185                 190

Gln Leu Glu Ala Val Gln Ala Ala Gly Ala Leu Ala Glu Gly Glu Leu
        195                 200                 205

Pro Lys Lys Asp Val Pro Gly Glu Gly Lys Glu Asp Gln Lys Ala Glu
        210                 215                 220

Gly Ala Asn Glu Val Asn Pro Lys Asn Glu Gln Tyr Ile Asn Asp Leu
225                 230                 235                 240

Glu Lys Ala Leu Arg Asp Phe Lys Ile Leu Ser Glu Ala Tyr Glu Asp
                245                 250                 255

Glu Lys Ser Leu Arg Arg His Gly Ser His Ser Gln Ser Glu Glu Asp
                260                 265                 270

Glu Thr Ser Ser Glu Glu Leu Asn Ser Gly Ser Asp Glu Asp Glu Glu
            275                 280                 285

Glu Asn Glu Glu Glu Glu Gln Pro Val Lys Asp Ser Gly Arg Lys Lys
290                 295                 300

Lys Arg Ser Lys Asp Ser Glu Glu Asp Ala Glu Asp Ala Ser Glu Glu
305                 310                 315                 320

Glu Leu Leu Lys Glu Thr Lys Ser Lys Ser Ala Asn His Asn Val Lys
                325                 330                 335

Glu Asn Thr Pro Pro Ala Glu Ser Thr Ile Thr Ser Lys Glu Ser Thr
                340                 345                 350

Lys Ser Ser Lys Gln Val Arg Arg Arg Pro Lys Lys Val
            355                 360                 365

<210> SEQ ID NO 33
<211> LENGTH: 365
<212> TYPE: PRT
<213> ORGANISM: Artificial Sequence
<220> FEATURE:
<223> OTHER INFORMATION: resistance to inhibitors of cholinesterase
      protein 3.1 [Haemonchus contortus]

<400> SEQUENCE: 33

Met Pro Val His Gly Arg Glu Arg Glu Arg Lys Arg Arg Arg Arg
1               5                   10                  15

Ser Asp Ser Glu Asp Asp Glu Ser Val Phe Thr Gly Trp Lys Leu Gly
            20                  25                  30

Leu Val Gly Val Ile Val Ile Cys Phe Ala Met Leu Tyr Pro Thr
        35                  40                  45

Leu Ile His Pro Met Leu Met Ser Leu Leu Gly Arg Ser Pro Pro
    50                  55                  60

Pro Pro Ala Val Pro Ser Arg Pro Pro Ile His Pro Gly Met Gly Gly
65                  70                  75                  80

Pro Gly Gly Gly Arg Pro Gly Gly Pro Ser Arg His Asp Val His Pro
                85                  90                  95

Ala Met Arg Met Ala Gln Gln Gln Ala Glu Thr Gln Ser Ser Gly Arg
            100                 105                 110

Gly Ser Phe Thr Trp Met Leu Pro Leu Tyr Thr Val Gly Val Val Ile
        115                 120                 125

Phe Leu Leu Tyr Thr Leu Phe Lys Ser Lys Gly Lys Arg Lys Arg Arg
    130                 135                 140

Ser Arg Tyr Gly Ser Ser Asp Glu Ser Ser Asp Asp Asp Val Tyr
145                 150                 155                 160

Asn Ser Arg Leu Lys Lys Lys Ile Gly Lys Arg Lys Leu Arg Ser Leu
                165                 170                 175

Gln Glu Arg Leu Gln Gln Thr Glu Glu Ala Met Ser Lys Ile Leu Glu
            180                 185                 190

Gln Leu Glu Ala Val Gln Ala Ala Gly Ala Leu Ala Glu Gly Glu Leu
        195                 200                 205

Pro Lys Lys Asp Ala Pro Gly Glu Gly Lys Glu Asp Gln Lys Ala Glu
    210                 215                 220

Gly Ala Asn Glu Val Asn Pro Lys Asn Glu Gln Tyr Ile Asn Asp Leu
225                 230                 235                 240

Glu Lys Ala Leu Arg Asp Phe Lys Ile Leu Ser Glu Ala Tyr Glu Asp
                245                 250                 255

Glu Lys Ser Leu Cys Arg His Gly Ser His Ser Gln Ser Glu Glu Asp
            260                 265                 270

Glu Thr Ser Ser Glu Glu Leu Asn Ser Gly Ser Asp Glu Asp Glu Glu
        275                 280                 285

Glu Asn Glu Glu Glu Glu Gln Pro Val Lys Asp Ser Gly Arg Lys Thr
    290                 295                 300

Lys Arg Ser Lys Asp Ser Glu Asp Ala Glu Asp Ala Ser Glu Glu
305                 310                 315                 320

Glu Leu Leu Lys Glu Thr Lys Gly Lys Ser Ala Asn His Asn Val Lys
                325                 330                 335

Glu Asn Thr Pro Pro Ala Glu Ser Thr Val Thr Ser Lys Glu Ser Thr
            340                 345                 350

Lys Ser Ala Lys Gln Val Arg Arg Pro Lys Lys Val
        355                 360                 365

MAMMALIAN CELL LINES EXPRESSING FUNCTIONAL NEMATODE ACETYLCHOLINE RECEPTORS AND USE THEREOF FOR HIGH-THROUGHPUT SCREENING ASSAYS

INCORPORATION BY REFERENCE

This application claims priority to U.S. provisional application No. 62/047,822, filed on 9 Sep. 2014, which is herein incorporated by reference in its entirety. All the documents cited herein are incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is MER 14-243 Seq Listing_ST25.txt. The text file is 99 KB; it was created on 8 Sep. 2015, based in large part upon the above-referenced provisional application; and it is being submitted electronically via EFS-Web, concurrent with the filing of the specification.

FIELD OF THE INVENTION

The disclosure generally relates to the production of mammalian cells lines, which express functional ion channels from heterologous species. The disclosure further relates to use of the stable cells lines for high throughput screening assays to identify compounds useful in modulating these receptors.

BACKGROUND OF THE INVENTION

Several commercial anthelmintic drugs (e.g. levamisole, pyrantel, morantel, monepantel, derquantel) disrupt the acetylcholine signaling pathway by agonizing or antagonizing AChRs in parasitic gastrointestinal (GI) nematodes of ruminants. However, GI parasite populations that are resistant to traditional anthelmintics, including cholinergic anthelmintics, are spreading globally and cause significant losses in farm productivity and profitability each year. One strategy to overcome current and minimize or prevent new resistance is to develop an anthelmintic with a novel mode of action. Ongoing research continues to identify and characterize additional components of the ACh signaling pathway in nematodes. Based on the precedent for the anthelmintic effectiveness of drugs that target ACh signaling, other components of the ACh signaling pathway may be exploited as novel anthelmintic targets.

ACR-16 is a homopentameric, levamisole-insensitive nicotinic acetylcholine receptor (nAChR) similar to the human alpha-7 nicotinic AChR that is found in neuromuscular junctions of both free-living and parasitic nematodes. ACR-16 functions as a ligand-gated ion channel that likely regulates fast action of acetylcholine at neuromuscular junctions and in the nervous system. In 2005 and 2007, Touroutine et al. showed that a "gain-of-function" mutation in ACR-16 was lethal to the free-living nematode *Caenorhabditis elegans* (Cel), and that ACR-16-containing receptors account for all non-levamisole sensitive nicotinic synaptic signaling at the Cel neuromuscular junction. These observations suggest that ACR-16 plays a vital role in nematode physiology, which led us and several other research groups to hypothesize that an agonist or positive allosteric modulator of ACR-16 could impair parasitic nematode physiology and, thus, be an effective anthelmintic.

RIC3 (resistance to inhibitors of cholinesterase 3) is a chaperone protein that in humans is encoded by the RIC3 gene. The RIC3 gene was first discovered in *C. elegans*, and influences the maturation of various ligand-gated ion channels including the serotonin 5-HT3 receptor and nicotinic acetylcholine receptors, particularly the homomeric α7 nicotinic receptor. RIC3 enhances currents generated by these receptors by expediting receptor transport to the cell surface and by increasing receptor number. Before the instant disclosure, the importance of RIC3 expression in yielding functional ACR-16-containing channels in cells was not appreciated.

*Haemonchus contortus* (Hco), also known as the barber's pole worm, is a blood-feeding, parasitic GI nematode and one of the most pathogenic nematodes of ruminants. Adult worms attach to abomasal mucosa and feed on blood, which causes anemia, edema, and death of infected cattle, sheep and goats, mainly during summer months in warm, humid climates. Adult female Hco may lay over 10,000 eggs a day, which pass from the host animal in the feces. After hatching from their eggs, Hco larvae molt several times to the infective larval stage 3 (L3), which is ingested by host animals during grazing. Ingested larvae mature to the adult stage in the host GI tract and ultimately attach to the abomasal mucosa.

Hco infection, or haemonchosis, causes large economic losses for farmers globally, but, especially for those living in warmer climates. Anthelmintics are used to treat and control ruminant GI infections of Hco and other parasitic nematodes, but growing resistance of parasites to anthelmintics such as levamisole and monepantel has rendered nematode control strategies extremely challenging, if not ineffective. Accordingly, a critical need exists to develop new anthelmintics against GI parasitic nematodes with novel modes of action.

In addition to GI parasites of ruminants, novel anthelmintics are needed for other parasitic nematode species have developed resistance to commercial anthelmintics. One important example is *Dirofilaria immitis* (Dim), a filarial nematode transmitted by mosquitoes that causes heartworm disease in dogs, cats, ferrets, and wild canids. Heartworm disease is a serious and potentially fatal condition caused by the adult stage of Dim that affects the right side of the heart and pulmonary arteries. Heartworm larvae are transmitted year-round. Although heartworm disease is most prevalent in warmer climates (with higher mosquito populations), it has been diagnosed in all fifty US states and throughout southern Europe. Commercial heartworm disease preventives work by interrupting the parasite life cycle within the host, thereby preventing the development of adult worms and associated pathology. Only one chemical class, the macrocyclic lactones (MLs), is approved by the FDA and other global agencies for the prevention of heartworm disease.

Since 2005, the existence of Dim subpopulations that are resistant to MLs populations in the US has been confirmed. These populations appear to be localized, mostly to the Mississippi Delta region of the US, though transportation of pets and shelter dogs across state lines or even internationally puts other regions at risk. Both the inherent mechanism(s) of Dim resistance to MLs and the potential of ML resistance to spread are unknown. Thus, an urgent need exists to develop new heartworm disease preventives with novel modes of action.

REFERENCES

Touroutine D et al., acr-16 encodes an essential subunit of the levamisole-resistant nicotinic receptor at the *Caenorhabditis elegans* neuromuscular junction. J. Biol Chem. 2005; 280(29): 27013-27021

Touroutine D et al., ACR-16 is an essential subunit of the levamisole-insensitive receptor. International Worm Meeting 2005.

SUMMARY OF THE INVENTION

In one aspect, the disclosure provides new and useful mammalian cells lines which have been genetically engineered to express functional nematode acetylcholine receptors from Hco or Dim. At the time of this disclosure, applicants are unaware of anyone successfully expressing functional nematode channels, not only ACR-16, in mammalian cells. Applicants are also unaware of any previous successful expression of functional Hco or Dim ACR-16 in any cell system, transiently or stably. This lack of success in the field can be explained by Applicants' surprising finding that, while co-expression of the obligate chaperone protein, RIC3, derived from either human or Hco, was sufficient to achieve functional Hco ACR-16 expression in mammalian cells, co-expression of Hco ACR-16 and *C. elegans* (Cel) RIC3 fails to yield a functional Hco ACR-16 channel. Moreover, and also quite unexpectedly, co-expression of Cel ACR-16 and Cel RIC3 did show functional responses. Accordingly, the knowledge in the field at the time of this disclosure, combined with applicants' unexpected results, support the nonobviousness of their invention.

Similarly, applicants have successfully generated a stable inducible HEK cell line co-expressing Dim ACR-16 and Dim RIC3 proteins that results in expression of a functional ACR-16 channel. Although applicants are aware of Hco ACR-16 being cloned previously, Applicants identified and cloned a novel, previously unknown ortholog expressed by Dim larvae.

In another aspect, the disclosure provides for ACR-16 functional validation and high-throughput screening assays. To the applicants' knowledge, no nematode species ACR-16 has ever been subjected to a large-scale, systematic screen for new active compounds. As indicated, nematodes have become increasingly resistant to parasiticides, making the search for new, safe and effective active ingredients essential to the future of our food supply.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, wherein:

FIG. 2 shows a map of the *Haemonchus contortus* (Hco) ACR-16/Human RIC3 construct;

DETAILED DESCRIPTION OF THE INVENTION

Figure 1:
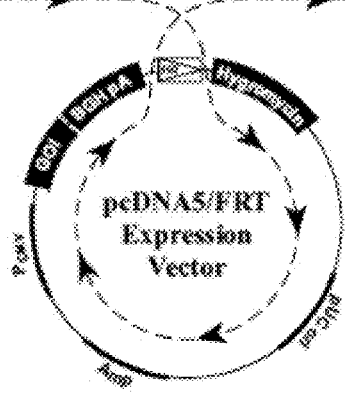
FIG. 1 shows a scheme for using the Flip-In-T-REX system.

The present invention relates to the production of mammalian cells lines, which express functional ion channels comprised of subunits from heterologous species. The disclosure further relates to use of the stable cells lines for high throughput screening (HTS) assays to identify compounds useful in modulating these receptors.

In a first aspect, the present invention provides a stable cell line that stably expresses both a gene encoding a nematode ACR-16 protein and a gene encoding a RIC3 protein. The presence of the RIC3 protein may be necessary for the expression of a resulting functional heterologous ion channel, which comprises the ACR-16 protein. As used herein, "ACR-16 protein" is equivalent to and used interchangeably with "acetylcholine receptor subunit ACR-16."

In an embodiment of the first aspect, the stable cell line contains within its genomic DNA and stably expresses both a gene encoding a functional heterologous nicotinic acetylcholine receptor (nACR) subunit protein, and a gene encoding a functional resistance to inhibitors of cholinesterase 3 (RIC3) protein. As a result of the stable expression of these two genes, the cell line expresses a functional ion channel comprising the heterologous nACR protein or subunit. In a particular embodiment, the nACR protein or subunit is an ACR-16 protein, also referred to herein as an "acetylcholine receptor subunit ACR-16."

In another embodiment, the stable cell line is produced by transfecting a human embryonic kidney (HEK) cell, or another mammalian cell, and selecting for stable recombinant cells.

In yet another embodiment, the stable cell line contains and expresses a gene encoding a nematode ACR-16 protein or subunit. The ACR-16 protein may have a sequence having at least 90% identity to a sequence as set forth in SEQ ID NO: 2, 19, 8, 20, 21, 22, 23, 24, 13 or 25, with the proviso that the ACR-16 protein forms part of the functional ion channel.

When percent identity language is used herein, it is to be understood that the protein or nucleic acid having substantial identity, at either the polypeptide sequence or polynucleotide sequence level, to one of the exemplified proteins or nucleic acids, must still exhibit sufficient structural and/or functional similarly to serve a substantially equivalent function as the exemplified protein or nucleic acid. For example, "an ACR-16 protein having at least 90% identity to the polypeptide sequence as set forth in SEQ ID NO: 2" means that the referenced non-identical protein must have at least 90% of the same amino acids in the same locations, relative to SEQ ID NO: 2, and it also means that the non-identical protein must serve the substantially similar function of being able to form part of a functional nACR ion channel.

Similarly, implicit in statements as to polynucleotide sequence identity is the understanding that the referenced non-identical nucleic acids must have substantial functional equivalence to the exemplified nucleic acids. Here, substantial functional equivalence of nucleic acids means that they encode for cognate polypeptides having substantial functional equivalence to one another. Accordingly, "an ACR-16 gene having at least 80% identity to the polynucleotide sequence as set forth in SEQ ID NO: 1" means that the referenced non-identical nucleic acid must have at least 80% of the same nucleotides in the same locations, relative to SEQ ID NO: 1, and it also means that the non-identical nucleic acid must serve the substantially similar function of coding for a protein that is able to form part of a functional ACR-16-containing nACR ion channel.

In yet another embodiment of the stable cell line, the stably-expressed ACR-16 protein has the sequence as set forth in SEQ ID NO: 2, 19, 8, 20, 21, 22, 23, 24, 13 or 25.

In another embodiment, the stable cell line contains and expresses a gene encoding for a RIC3 protein having at least 90% identity to the sequence as set forth in SEQ ID NO: 4, 26, 27, 28, 29, 30, 31, 6, 32, 33, 10 or 16. In an embodiment, the RIC3 protein has a polypeptide sequence having the sequence as set forth in SEQ ID NO: 4, 26, 27, 28, 29, 30, 31, 6, 32, 33, 10 or 16.

In a particular embodiment, the ACR-16 and RIC3 proteins are *Haemonchus contortus* (*H. contortus*) and *Homo sapiens* proteins, respectively.

In another particular embodiment, both the ACR-16 and the RIC3 proteins are *H. contortus* proteins. The ACR-16 and RIC3 proteins may also both be *Dirofilaria Immitis* (*D. immitis*) proteins.

In one embodiment, the ACR-16 protein is a *D. immitis* protein and the RIC3 protein is a human RIC3 protein.

In another embodiment, the ACR-16 protein is a *D. immitis* protein and the RIC3 protein is a *H. contortus* protein.

In a second aspect, the disclosure provides a high throughput screening (HTS) method for identifying modulators of ACR-16-containing channels In an embodiment, the HTS method may comprise the general steps of:

a) culturing the disclosed stable cell lines that express functional ACR-16-containing ion channels;

b) exposing aliquots of the stable cells to control and experimental compounds; and c) determining which experimental compounds are able to modulate the activity of the ACR-16-containing ion channel, thereby identifying modulators of the ACR-16-containing ion channel.

In one embodiment, the determining step may comprise the step of measuring a significantly greater or lesser amount of calcium influx in the experimental aliquots of cells, relative to the amount of calcium influx in the control aliquots of cells.

In a particular embodiment of the method, the calcium influx may be determined to be significantly greater in the experimental cells, indicating that the modulators are agonists of the ACR-16-containing ion channel. In an embodiment, the agonists are safe and effective parasiticidal agents for administration to animals in need thereof.

In a third aspect, the disclosure provides at least one vector for producing the ACR-16- and RIC3-expressing stable cell lines.

In an embodiment, the vector comprises both a gene encoding a heterologous nicotinic acetylcholine receptor (nACR) protein and a gene encoding and a resistance to inhibitors of cholinesterase 3 (RIC3) protein. The vector may contain a variety of elements known to those of skill in the art. For example, it is routine practice to incorporate antibiotic resistance cassettes, promoters, enhancers, transcription terminators, origins of replication, and any other elements required for gene expression, plasmid production/replication, and selection of stable recombinant cells. Now that the inventive combinations of ACR-16 and RIC3 have been disclosed, Applicants envision that a wide range of DNA vectors, including plasmid vectors, may be employed to produce a wide range of stable cells lines, including stable HEK cells. The stable cell line of the disclosure may be produced using the reagents and techniques disclosed herein, or they may be made using any other routine methods known by those of skill in the art.

In another embodiment, the vector contains a gene encoding a functional nematode ACR-16 protein and a gene encoding a functional RIC3 protein. The gene encoding the RIC3 protein may be selected from a human RIC3 gene, an *H. contortus* RIC3 gene, a *C. elegans* RIC3 gene and a *D. immitis* RIC3 gene. Since applicants have surprisingly found that vectors containing an Hco ACR-16 gene and a *C. elegans* RIC3 gene fail to produce stable cells expressing functional ACR-16-containing channels, a non-*C. elegans* RIC3 gene is preferred when an Hco ACR-16 gene is present in the vector.

In still another embodiment of the vector, the ACR-16 gene has at least 80% identity to the sequence as set forth in SEQ ID NO: 1, 7, 11 or 12 and the RIC3 gene has at least 80% identity to the sequence as set forth in SEQ ID NO: 3, 5, 9, 14 or 15, in any combination of ACR-16 gene and RIC3 gene, with the proviso that when the vector contains an Hco ACR-16, the RIC3 gene is not a *C. elegans* RIC3 gene.

The ACR-16 gene may also have a polynucleotide sequence that encodes a polypeptide as set forth in SEQ ID NO: 2, 19, 8, 20, 21, 22, 23, 24, 13 or 25. Alternatively, the ACR-16 gene may encode a polypeptide that is at least 90% identical to a polypeptide sequence as set forth in SEQ ID NO: 2, 19, 8, 20, 21, 22, 23, 24, 13 or 25.

In another embodiment of the vector, the ACR-16 gene has the sequence as set forth in SEQ ID NO: 3, 5, 9, 14 or 15; and the RIC3 gene has the sequence as set forth in SEQ ID NO: 3, 5, 9, 14 or 15. Any combination of ACR-16 gene and RIC3 gene is envisioned, with the proviso that when the vector contains an Hco ACR-16, it is preferred that the RIC3 gene be other than a *C. elegans* RIC3 gene.

In yet another embodiment, the RIC3 gene may encode a polypeptide as set forth in SEQ ID NO: 4, 26, 27, 28, 29, 30, 31, 6, 32, 33, 10 or 16. The RIC3 gene may also encode a polypeptide having at least 90% identity to a polypeptide as set forth in SEQ ID NO: 4, 26, 27, 28, 29, 30, 31, 6, 32, 33, 10 or 16.

In a particular embodiment of the vector, the ACR-16 gene has the sequence as set forth in SEQ ID NO: 1 and the RIC3 gene has the sequence as set forth in SEQ ID NO: 3.

In a fourth aspect, the disclosure provides a method for producing cells that stably express functional ACR-16-containing ion channels, which comprises the step of stably transfecting cells with both an ACR-16 gene and a RIC3 gene. In a particular embodiment, the ACR-16 gene has the sequence as set forth in SEQ ID NO: 1 and the RIC3 gene has the sequence as set forth in SEQ ID NO: 3.

The invention will now be further described by way of the following non-limiting examples.

EXAMPLES

Below discloses the development of the disclosed stable cell lines, which express functional ACR-16 channels, and are useful for the high-throughput screening of compounds capable of modulating ACR-16 channel function.

Example 1—Production of Mammalian Cells Expressing Functional Nematode AChR: Hco ACR-16/Human RIC3

Materials & Methods.

In general, the Flp-In™ T-Rex™-293 (Human Embryonic Kidney cells) and the Flp-In™ T-Rex™ system # FITR were used to produce the stable cell lines. The vector was pCDNA5-FRT-TO_DEST and the insert sequences were Hco ACR-16 (SEQ ID NO: 1) and Human RIC3 (SEQ ID NO: 3) (depicted in FIG. 2). Cells were grown in DMEM (#31966, Invitrogen) supplemented with 10% FCS (#10500, Gibco), 15 µg/ml Blasticidin (#ant-bl-1, InVivoGen) and 80 µg/ml Hygromycin B (#10867, Invitrogen). Cells were grown at 37° C., 5% CO2 and 90% humidity, and passaged using Accutase (#091000449, Sigma). Finally, inductions were carried out using 0.1 µg/ml doxycycline at for 24 h at 37° C.

Figure 2:
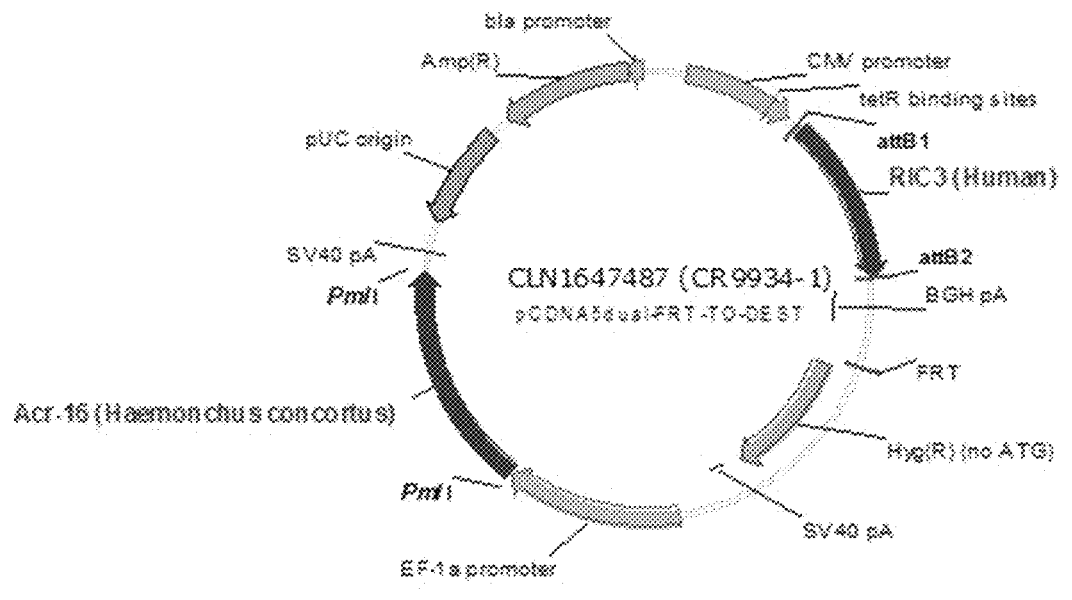

The Flp-In™ T-Rex™ expression system allows the generation of stable mammalian cell lines. The gene of interest can be integrated at a specific genomic location called Flp Recombination Target (FRT) site. The integration of the gene of interest into the genome is mediated through a Flp recombinase. With this system, the generation of stable cell line is rapid and efficient as it permits the generation of isogenic cell lines without clonal selection. This system is illustrated in FIG. 2, 19, and is available in more detail in the product manuals for pcDNA™5/FRT/TO (herein incorporated by reference in their entirety. The inducible expression vector was designed for use with the Flp-In™ T-REx™ System (Cat. no. V6520-20).

The *Haemonchus contortus* ACR-16 clone was obtained from the University of Manchester and was back-mutated to match the publicly available accession number. The following primers were then used to equip the clone with suitable restriction sites for cloning into pCDNA5dual-FRT-TO_D-EST. Cloning was done using the InFusion technology. SEQ ID NO:17 (9924-01 forward primer PmlI InFusion) 5'-AGG TGT CGT GAA CAC GTG CCA CCA TGT GGA GCT TGC TGA TCG C-3'; SEQ ID NO:18 (9924-02 reverse primer PmlI InFusion) 5'-AGC GGC CGC GAC CAC GTG CTA GGC GAC CAG ATA TGG AG-3'. The human RIC3 was taken from a clone that was cloned from adrenal tissue at Sanofi. For cloning into pCDNA5 dual-FRT-TO_DEST, the Gateway cloning technology was used.

Transfections. One day prior to transfection, $1.5*10^6$ Flp-In-T-Rex-293 or —CHO cells were seeded in 10 ml DMEM or HAM-F12 containing 10% FCS into a Petri Dish (ø=100 mm) and incubated at 37° C./10% CO2 overnight. Using the Lipofectamine transfection reagent, cells were co-transfected with the Flp recombinase expression plasmid pOG44 and the pCDNA5 dual-FRT-TO-target with a 9:1 ratio. For the transfection of one dish, 10.8 µg of pOG44 and 1.2 µg of pCDNA5 dual-FRT-TO-target were mixed to 500 µl Opti-MEM I medium containing 72 µl Lipofectamine reagents. After 20 minutes of incubation at room temperature, the transfection reagent/DNA complex was distributed drop wise onto the cells. Flp-In-T-Rex-293 or —CHO cells were incubated at 37° C./10% CO2. Five hours after transfection the cells were washed and fresh culture medium was added to the cells.

Forty-eight hours after transfection the cells were washed and fresh cultivation medium containing the selection antibiotic was added. Flp-In-T-Rex-293-HcoACR-16 hRic3 cells were selected with 80 µg/ml hygromycin. The culture medium was exchanged every 2-3 days until a resistant population of cells had grown. After two to three weeks of selection, the cells were cultivated in T75 flasks for scale-up and batch production.

In parallel, a transitory expression of HcoACR-16 with Hco and Cel Ric3 was performed in the HEK parental cell line. The combination of Hco AChR-16+Cel Ric3 did not yield functional AChR16 channels while expression of HcoACR-16+Hco or human Ric3 did yield functional channels.

Cells were harvested from the culture flasks by a short treatment (2-5 minutes) with accutase, resuspended in culture medium and centrifuged at 1000 rpm/10 min. Cells were resuspended in 90% fetal calf serum containing 10% DMSO and stored frozen in liquid nitrogen. All cell lines in culture and in the frozen stock were *mycoplasma*-free. DMEM (Gibco 31966) supplemented with 10% FCS (Gibco 10500) and 100 µg/ml Penicillin & Streptomycin (Gibco 15140); 80 µg/ml Hygromycin B (Invitrogen 10687); and 15 µg/ml Blasticidin (InVivoGen ant-bl-1). Subculturing was performed by the following procedure: detach cells with Accutase (Sigma A6964), 1 ml/T75 cm2 flask Count: Vi-Cell (Beckman Coulter) Split Ratio: A subcultivation inoculum of 1:10 for 3 days maintenance and 1:15 for 4 days maintenance is recommended. Environment: 5% CO2/37° C./95% RH Culture Flasks: 75 cm² flask (Corning 430641).

Example 2—Production of Mammalian Cells Expressing Functional Nematode AChR: Hco ACR-16/Hco RIC3

Figure 3:
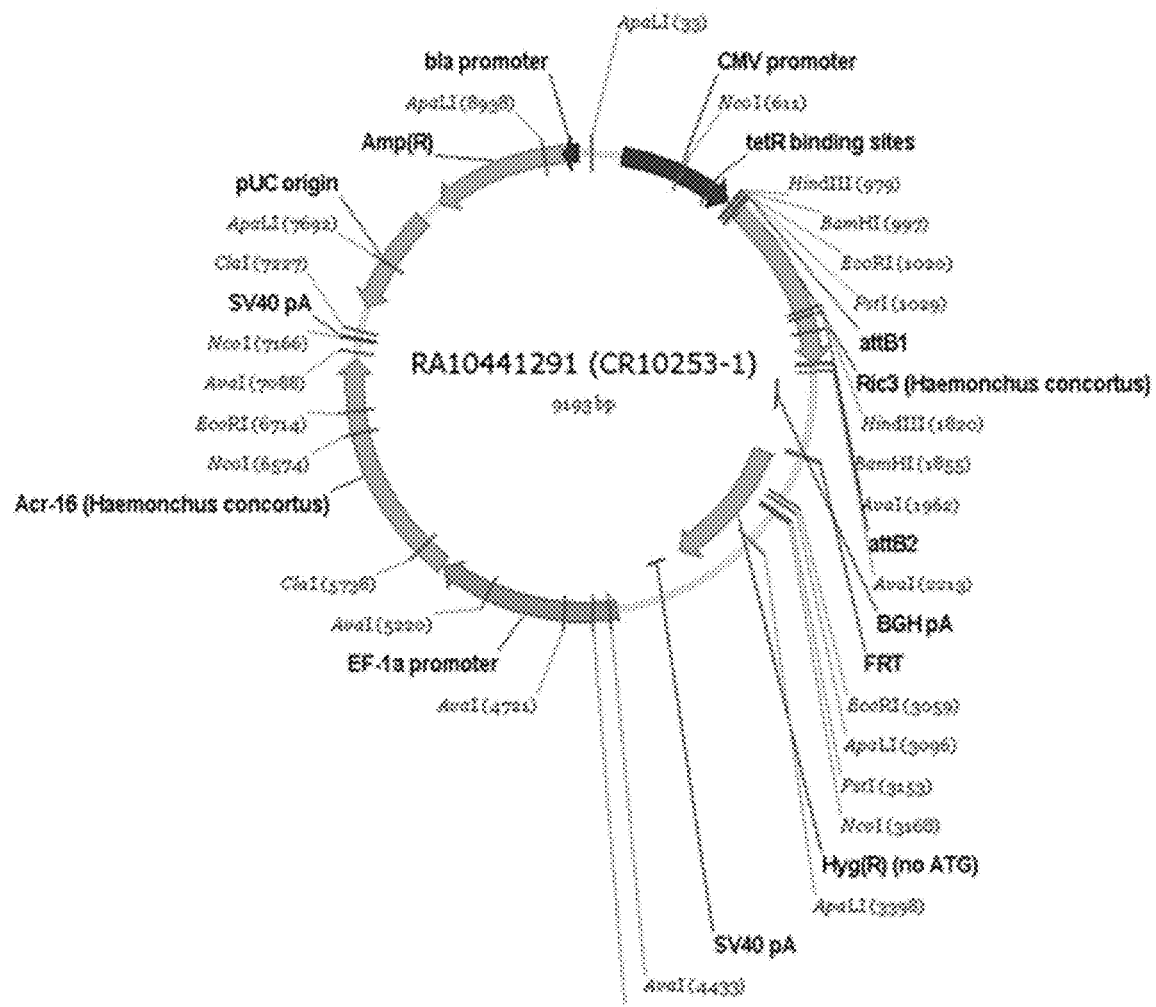
FIG. 3 shows a map of the Hco ACR-16/Hco RIC3 construct.

The methods of Example 1 were used, except that the insert sequences used were Hco ACR-16 (SEQ ID NO: 1) and Hco RIC3 (SEQ ID NO: 5) (depicted in FIG. 3).

Example 3—Production of Vectors for Transient Expression of Functional Nematode AChR: Cel ACR-16 and Cel RIC3

The methods of Example 1 were used, except that the vector was pCDNA3.1neo_DEST and the insert sequences were Cel ACR-16 (SEQ ID NO: 7) and Cel RIC3 (SEQ ID NO: 9). Transfections were carried out using FuGENE 6 (#E2691, Promega).

Example 4—Production of Mammalian Cells Expressing Functional Nematode AChR: Dim ACR-16/Dim RIC3

Figure 4:
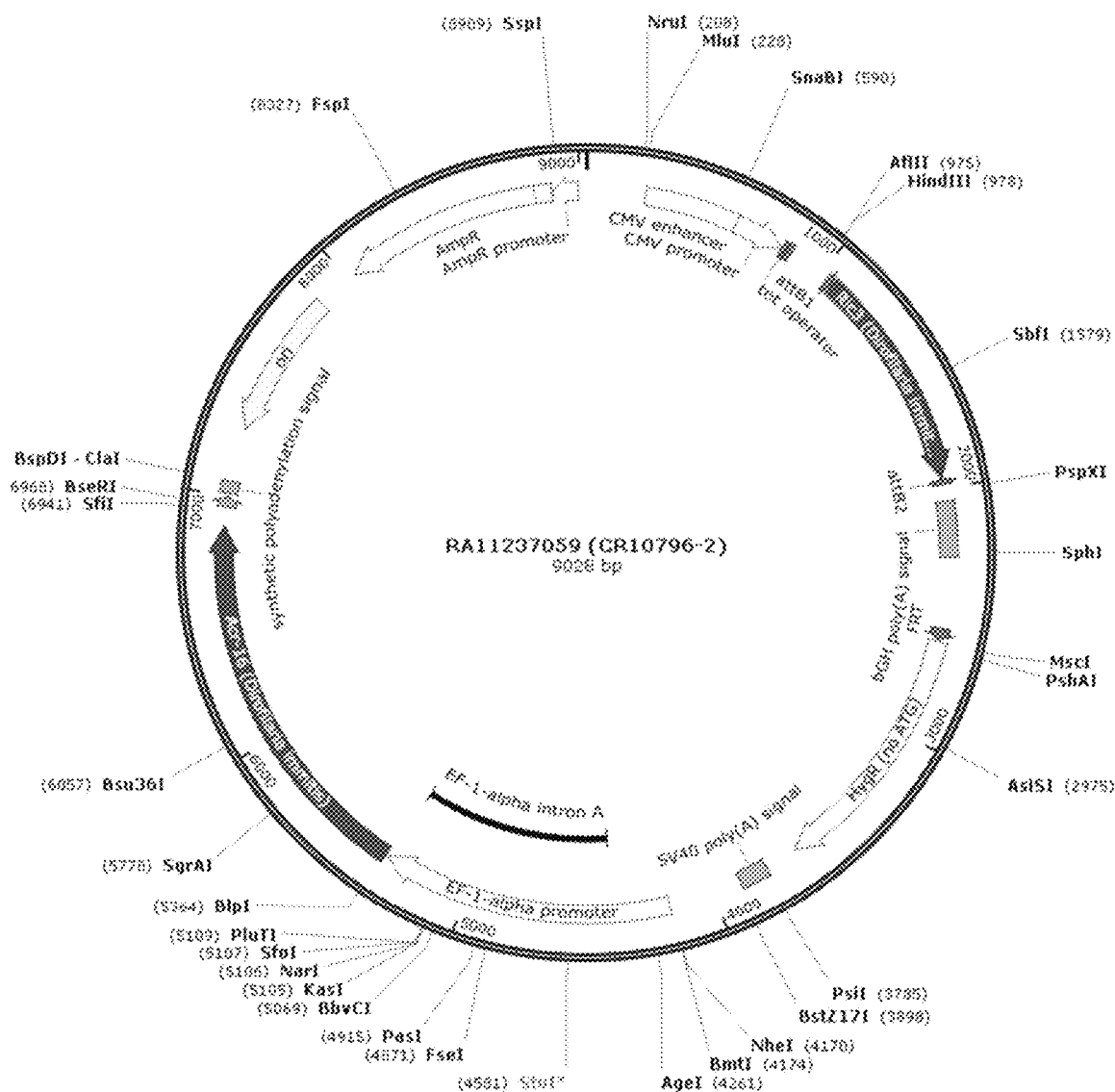
FIG. 4 shows a map of the Dim ACR-16/Dim RIC3 construct.
Figure 5:
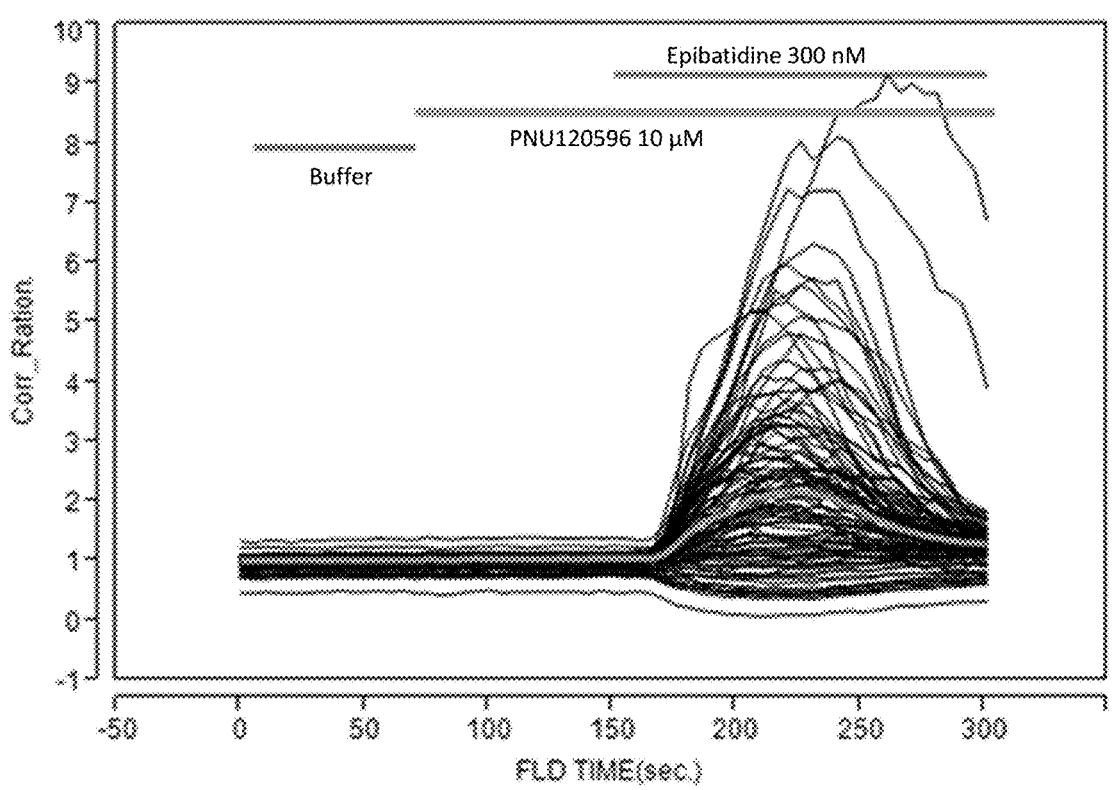
FIG. 5 shows video-imaging results for the Hco ACR-16/hRIC3 stable cell line (each line represents one individual cell). Highlighted are calcium signal levels obtained following application of buffer, 10 µM PNU120596, and 300 nM epibatidine.
Figure 6:
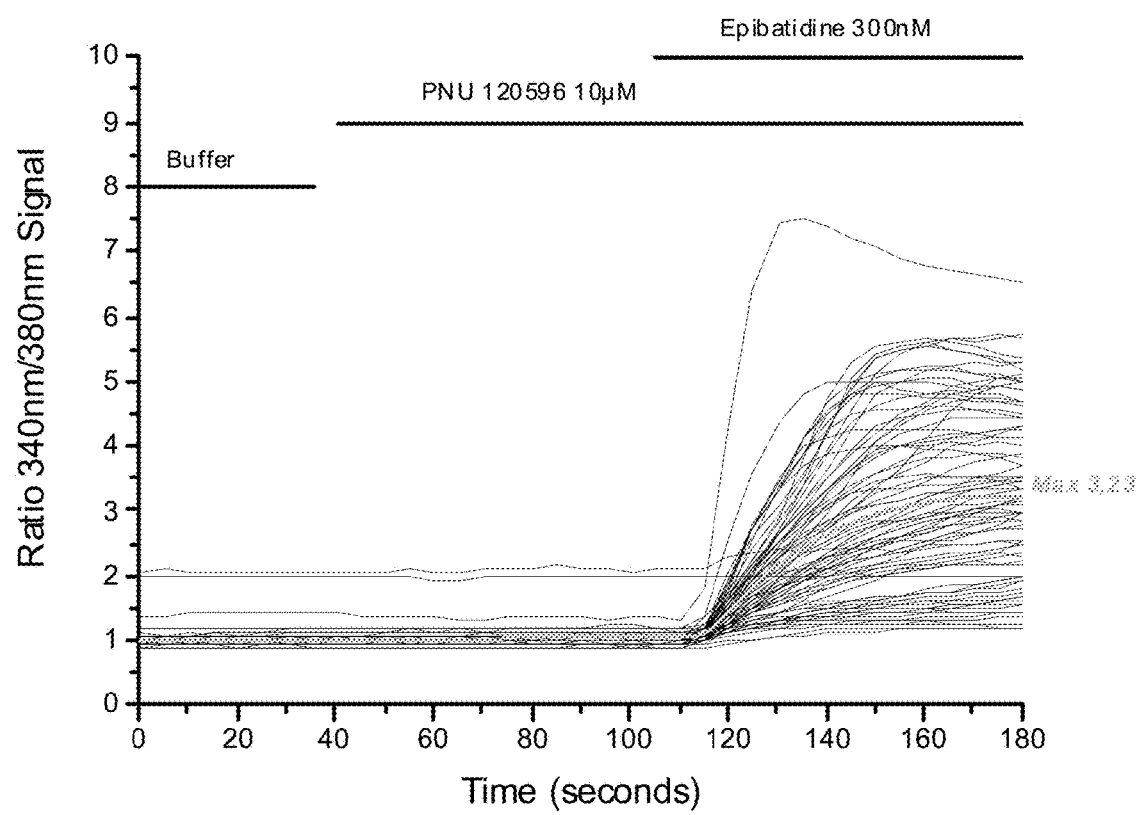
FIG. 6 shows video-imaging results for the Hco ACR-16/Hco RIC3 stable cell line. Highlighted are calcium signal levels obtained following application of buffer, 10 µM PNU120596, and 300 nM epibatidine.
Figure 7:
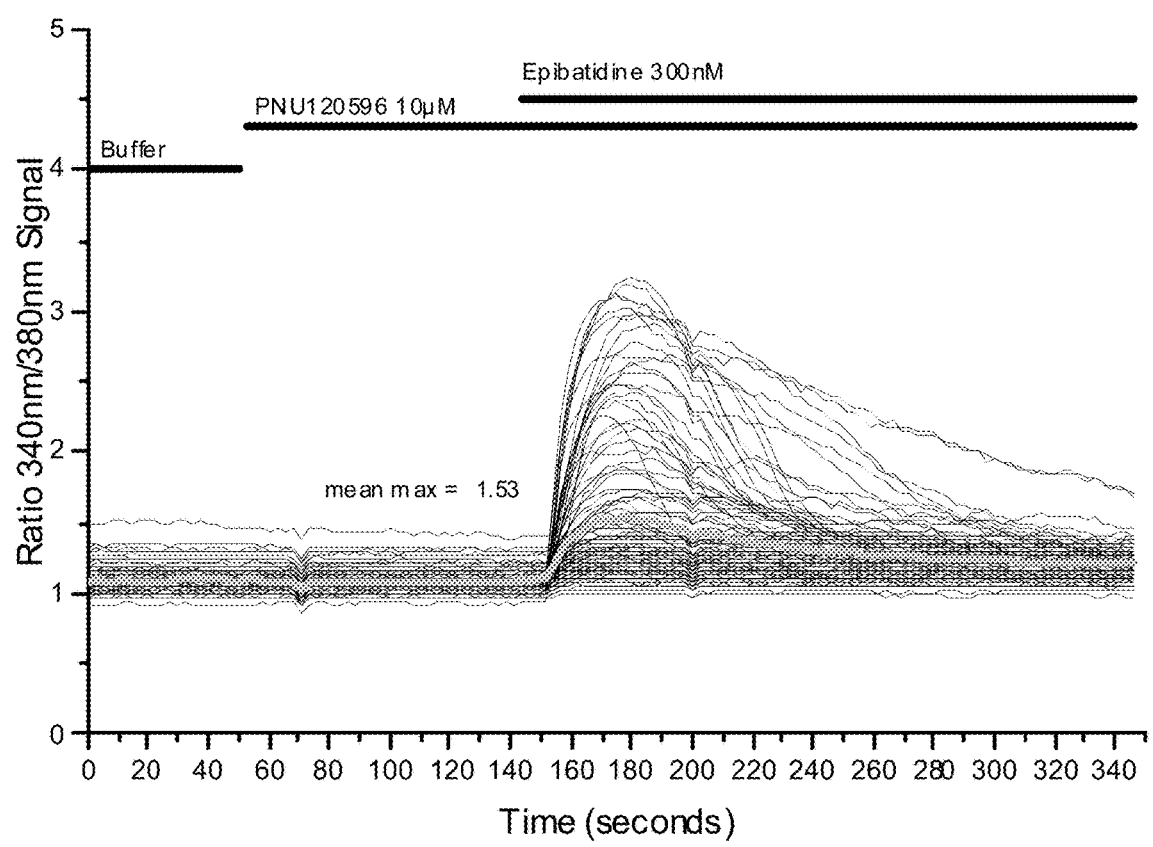
FIG. 7 shows video-imaging results for the Dim ACR-16/Dim RIC3 stable cell line. Highlighted are calcium signal levels obtained following application of buffer, 10 µM PNU120596, and 300 nM epibatidine.
Figure 8:
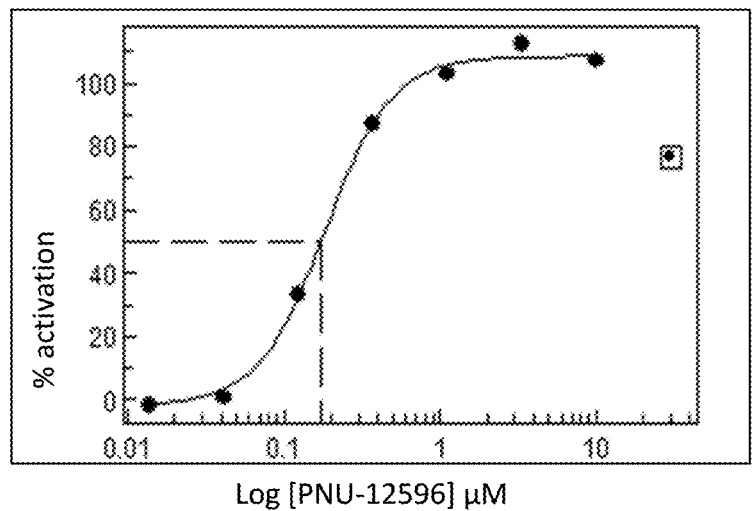
FIG. 8 shows PNU-120956 concentration-response curves fitted using a four-parameter logistic equation of the form $y=[A1-A2/(1+x/x0)p]+A2$, where A1 is the maximum asymptote, A2 is the minimum asymptote, x0 is the XC50, and p is the Hill slope. A value of 160 nM was calculated.
Figure 9:
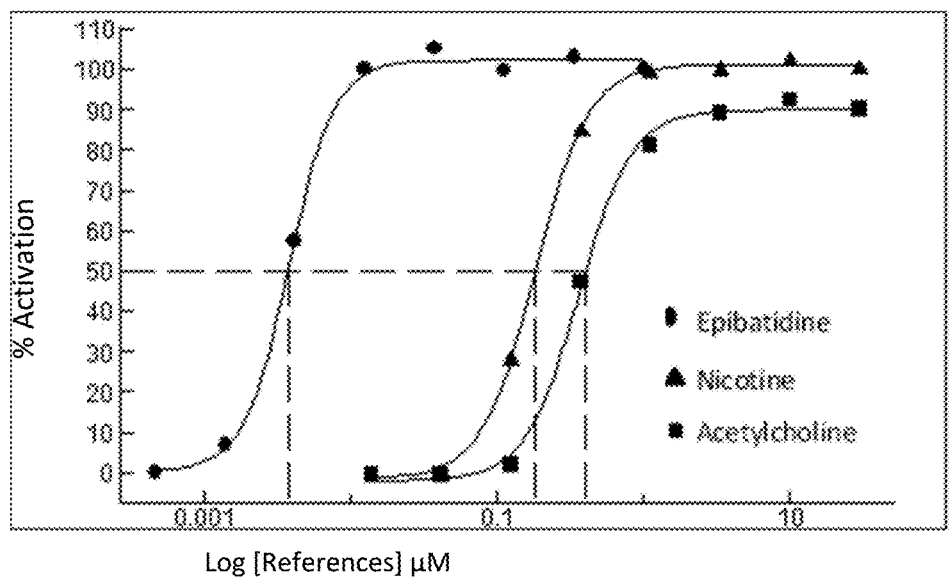
FIG. 9 shows concentration response curves for cells stably expressing Hco ACR-16/hRIC3 for three orthosteric reference agonists, epibatidine (6 nM), nicotine (200 nM) and acetylcholine (480 nM)
Figure 10:
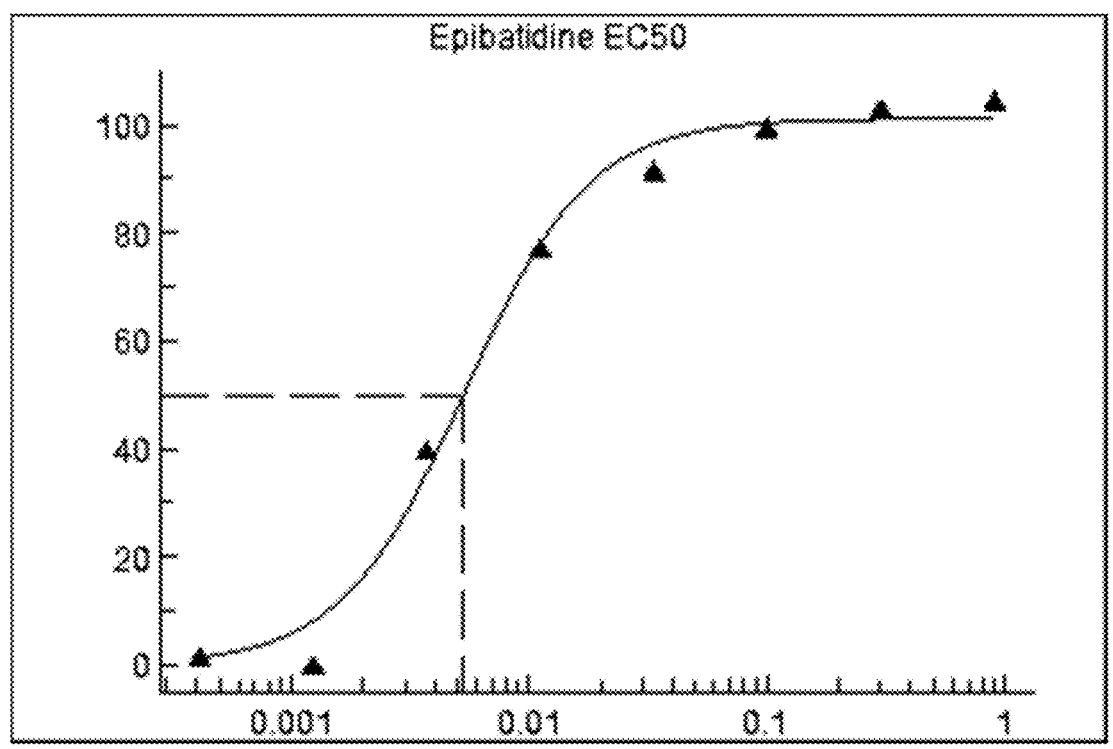
FIG. 10 shows the concentration response curve for Dim ACR-16/Dim RIC3 stable cells for an orthosteric reference agonist, epibatidine (EC50 10 nM)
Figure 11:
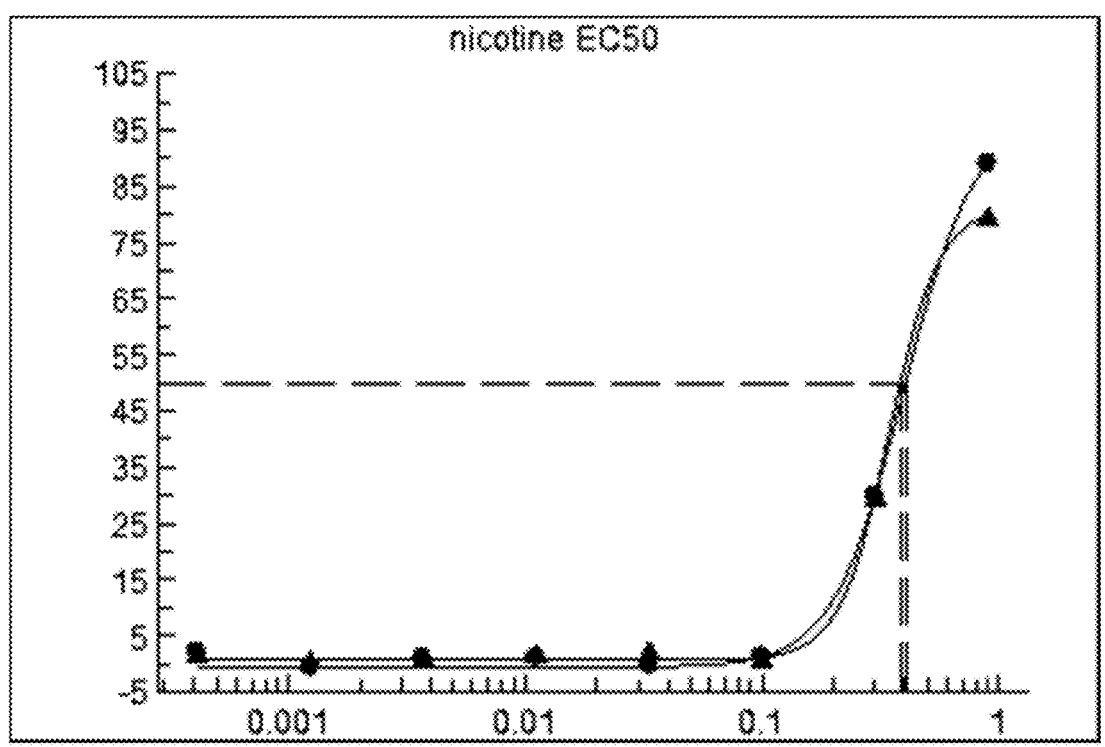
FIG. 11 shows the response curve for another orthosteric agonist, nicotine (EC50 350 nM)
Figure 12:
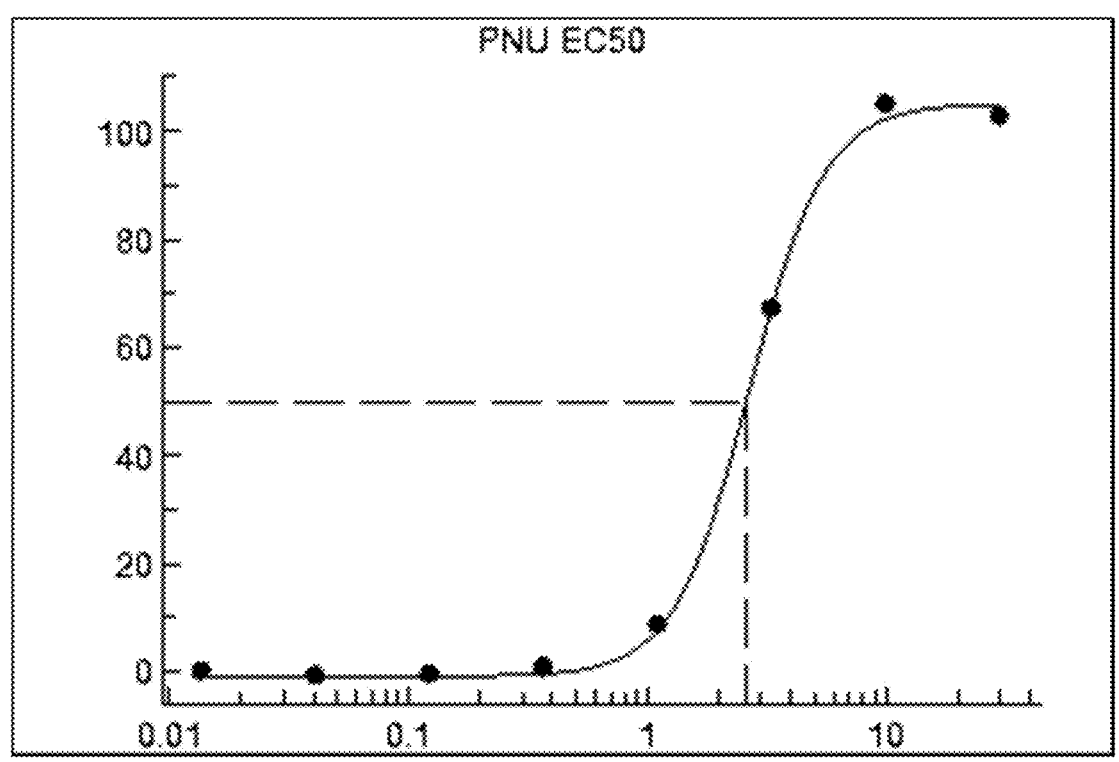
FIG. 12 shows the response curve for the allosteric modulator PNU120596 (EC50 2.4 µM).

As in Example 1, Flp-In™ T-Rex™-293 (Human Embryonic Kidney cells) and the Flp-In™ T-Rex™ system # FITR were used to produce the stable cell lines. The vector was pCDNA5-FRT-TO_DEST and the inserts were codon-optimized Dim ACR-16 (SEQ ID NO:12) and codon-optimized Dim RIC3 (SEQ ID NO:15) (depicted in FIG. 4). Applicants cloned Hco RIC3 from Hco cDNA prepared from field isolates, and to their knowledge, no one has previously published this sequence.

Example 5—Evaluation of Mammalian Cells Expressing Functional AChR Using Calcium Mobilization Fluorescence Assays Video-Imaging Setup, Assay Protocol for Fluorescence-Ca2+ Measurement Fluorescence intensity was measured on a Hamamatsu station (camera, polychromator, Simple PCI software) with two excitation wavelengths 340 (free fura2) & 380 nm (Ca2+-fura2) and emission beyond 510 nm.

Working Assay Buffer=Ringer's Solution:

In distilled water: to mM Hepes (Sigma H7523), 150 mM NaCl (Sigma S6191), 4 mM KCl (Sigma P5405), 2 mM $CaCl_2$ (Sigma C4901), 1 mM $MgCl_2$ (Sigma M2670), adjusted at pH 7.3 by NaOH 2M (Fisher). All products are in powder form except NaOH in solution form. Osmolarity was set up at 301 mmol/kg.

Assay Protocol for Video-Imaging Ca2+ Measurement:

$Ca^{2+}$ increase was monitored using Flura-2 (AM) dye and imagery of fluorescence was performed on a Hamamatsu platform (Nikon Eclipse TE2000U+Photonics Polychromator+Orca Camera+SimplePCI software).

Cells were seeded in growth medium with 1 μg/ml of doxycycline onto Labtek Chamber slideck, poly-lysine coated at a cell density of $200 \times 10^3$ cells/chamber in 1 mL.

Induction: doxycycline 1 μg/ml for 24 h @ 37° C. @ 5% $CO_2$,

1 μM of Fura-2-AM was added for 20 minutes at 37° C./5% $CO_2$

Medium was replaced by assay buffer (Ringer's solution).

Fluorescence intensity was measured above 510 nm with both excitation wavelengths of 340 (free-fura2) and 380 nm excitation ($Ca^{2+}$ bound fura2).

Calcium increase was triggered by reference agonist application: 300 nM epibatidine in assay buffer following pre-incubation of 10 μM PNU-120596.

TABLE 1

Reagents for the Calcium Imaging Studies

| Materials | Supplier | Cat. No. | Function |
|---|---|---|---|
| Flura-2 AM | Molecular Probes | F1221 | Calcium sensitive fluorescent dye |
| HEPES | SIGMA | H7523 | Ringer's Buffer solution |
| NaCl | SIGMA | S6191 | Ringer's Buffer solution |
| KCl | SIGMA | P5405 | Ringer's Buffer solution |
| $MgCl_2$ | SIGMA | M2670 | Ringer's Buffer solution |
| $CaCl_2$ | SIGMA | C4901 | Ringer's Buffer solution |
| NaOH | Fisher | | Ringer's Buffer solution pH adjusted |
| Epibatidine | SIGMA | P178 | nAChR agonist Reference |
| PNU120596 | | | nAChR positive allosteric modulator reference |
| Flp-In-293-Hco ACR-16 hRic3 | | | Cell line expressing the Hco ACR-16 and hRic3 (i.e. the line described in Example 1) |
| Flp-In-293 | | | Parental cell line |
| Poly-D-Lysine | SIGMA | P6407 | Coating |
| Lab-Tek II ® Chamber slide | NUNC | 155379 | Assay plate |

TABLE 2

Epibatidine statistics

| Event | Est. | N | Mean | Std Dev | Median | nMAD | Min | Max |
|---|---|---|---|---|---|---|---|---|
| Epibatidine 300 nM | Rmin | 98 | 1.02 | 0.12 | 1.04 | 0.07 | 0.49 | 1.39 |
| Epibatidine 300 nM | Rmax | 98 | 2.62 | 1.69 | 2.34 | 1.42 | 0.49 | 9.16 |
| Epibatidine 300 nM | Ratio | 98 | 2.51 | 1.57 | 2.15 | 1.31 | 0.99 | 8.10 |
| Epibatidine 300 nM | Reaction Time | 51 | 17.69 | 9.79 | 15.03 | 0.00 | 15.03 | 80.20 |
| Epibatidine 300 nM | AUC | 98 | 271.25 | 141.44 | 253.67 | 110.84 | 33.42 | 869.8 |

Assay Protocol for Ca2+ Measurement in 384-Well Plate Format on FDSS6000 (Hamamatsu)

The Ca$^{2+}$ increase through either Hco or Dim ACR-16 was monitored using Fluo-4AM dye and measured by a FDSS6000 platform (Hamamatsu). Twenty-four hours before the experiment, cells were seeded in growth medium into 384-well black, clear bottom poly-lysine coated plates, at a cell density of 10.000 cells/well in 50 µl complemented with 1 µg/ml doxycycline.

Medium was replaced by washing three times with assay buffer, keeping a residual volume of 25 µl per well. Subsequently 25 µl of dye loading buffer were added and the plate was incubated for 1 h at RT.

Dye loading buffer was removed by washing three times with assay buffer (Cell washer BioTek), keeping a residual volume of 50 µl per well.

Plates were transferred to the FDSS6000 reader and measured for agonist response by adding 5 µl of agonist solution.

TABLE 3

Calcium Imaging Reagents

| Materials | Supplier | Cat. No. | Function |
|---|---|---|---|
| Fluo-4/AM | Invitrogen | | Calcium sensitive fluorescent dye |
| HBSS (10x) with calcium/magnesium | Invitrogen | 14065 | Buffer solution |
| Flp-In-293-Hco ACR-16/hRIC3 hybrid | | | Cell line expressing ACR-16 |
| Epibatidine | | | nAChR agonist reference |
| PNU-120596 | | | nAChR positive allosteric modulator reference |
| 384-well plate (poly-lysine coated) | BD | | Assay plate |

TABLE 4

Assay Buffer Composition

| Reagent | Chemicals | Remarks |
|---|---|---|
| Assay buffer | HBSS (+Ca/+Mg) 1x<br>1 mM CaCl$_2$<br>20 mM Hepes<br>0.001% Pluronic acid<br>Set to pH 7.4 | |
| Agonist/compound buffer | Assay buffer | Fresh solution of epibatidine/nicotine was prepared |
| Dye loading buffer | Assay buffer containing:<br>4 µM Fluo-4/AM<br>0.1% BSA | Fluo-4/AM is added from a 0.5 mM stock solution in DMSO (1 mg diluted in 910 µl DMSO, protected from light) |

TABLE 5

Robustness values obtained for 384-w format assay using Hco ACR-16/hRIC3 cell line

| Conditions | Signal amplitude with 10 µM PNU120596 + 300 nM epibatidine application (RFU) | Z' |
|---|---|---|
| 24 h @ 37° C. | 1503 | 0.89 |
| 24 h @ 37° C. + 24 h @ 30° C. | 2160 | 0.90 |

As a measure of assay robustness, the Z' value is calculated as follows using the means (µ) and standard deviations (σ) of both positive (p) and negative (n) controls ($\mu_p$, $\mu_n$, $\sigma_p$ and $\sigma_n$):

$$Z'=1-3*(\sigma_p+\sigma_n)/|\mu_p-\mu_n|$$

For a high-throughput screen, a Z' value of 1 is ideal and greater than 0.5 is considered excellent. Z' is typically calculated for each plate with plate-specific positive and negative controls.

TABLE 6

EC50 values for reference compounds vs Hco ACR-16/hRIC3 cell line

| Reference compounds | EC50 value (µM) | Remarks |
|---|---|---|
| Epibatidine | 0.006 | Revealed by co-application of PNU-120956 |
| Nicotine | 0.20 | Revealed by co-application of PNU-120956 |
| Acetylcholine | 0.48 | Revealed by co-application of PNU-120956 |
| PNU-120956 | 0.16 | Revealed by co-application of EC100 orthosteric reference agonist |

TABLE 7

Robustness values obtained for 384-w format assay using Hco ACR-16/Hco RIC3 cell line

| Conditions | Signal amplitude with 10 µM PNU120596 + 300 nM epibatidine application (RFU) | Z' |
|---|---|---|
| 24 h @ 37° C. | 680 | 0.81 |
| 24 h @ 37° C. + 24 h @ 30° C. | 1601 | 0.85 |

TABLE 8

Hco ACR-16/Hco RIC3 stable cell line Result on FDSS6000 setup

| Reference compounds | EC50 value (µM) | Remarks |
|---|---|---|
| Epibatidine | 0.005 | Revealed by co-application of PNU-120956 |
| PNU-120956 | 1.4 | Revealed by co-application of EC100 orthosteric reference agonist |

TABLE 9

Dim ACR-16/Dim RIC3 stable cell line Results on FDSS6000 setup

| Reference compounds | EC50 value (µM) | Remarks |
|---|---|---|
| Epibatidine | 0.005 | Revealed by co-application of PNU-120956 |
| Nicotine | 0.4 | Revealed by co-application of PNU-120956 |
| PNU-120956 | 2.4 | Revealed by co-application of EC100 orthosteric reference agonist |

TABLE 10

Robustness values obtained for 384-w format assay using Dim ACR-16/Dim RIC3 cell line

| Conditions | Signal amplitude with 10 µM PNU120596 + 300 nM epibatidine application (RFU) | Z' |
|---|---|---|
| 24 h @ 37° C. + 24 h @ 30° C. | 450 | 0.81 |

The invention will now be set forth in the following non-limiting claims.

What is claimed:

1. A stable mammalian cell line that contains within its genomic DNA and stably expresses both a gene encoding a heterologous *Haemonchus contortus* (*H. contortus*) nicotinic acetylcholine receptor (nAChR) protein subunit ACR-16 and a gene encoding a *homo sapiens* resistance to inhibitors of cholinesterase 3 (RIC3) protein, such that the cell line expresses a functional ion channel comprising the heterologous *H. contortus* nAChR protein subunit ACR-16.

2. The stable cell line of claim 1, wherein the *H. contortus* ACR-16 protein has at least 95% identity to a sequence as set forth in SEQ ID NO: 2 or 19.

3. The stable cell line of claim 2, wherein the RIC3 protein has a polypeptide sequence having at least 90% identity to the sequence as set forth in SEQ ID NO: 4 or 27.

4. The stable cell line of claim 1, wherein the RIC3 protein has a polypeptide sequence having at least 90% identity to the sequence as set forth in SEQ ID NO: 4 or 27.

5. A vector for producing a stable mammalian cell line, comprising both a gene encoding a heterologous *H. contortus* nicotinic acetylcholine receptor (nAChR) protein subunit ACR-16 and a gene encoding the *homo sapiens* resistance to inhibitors of cholinesterase 3 (RIC3) protein.

6. The vector of claim 5, wherein the *H. contortus* ACR-16 gene has at least 95% identity to the sequence as set forth in SEQ ID NO: 1, and the RIC3 gene has at least 95% identity to the sequence as set forth in SEQ ID NO: 3.

7. The vector of claim 6, wherein the ACR-16 gene has the sequence as set forth in SEQ ID NO: 1 and the RIC3 gene has the sequence as set forth in SEQ ID NO: 3.

* * * * *